United States Patent
Bedi et al.

(10) Patent No.: US 12,138,114 B2
(45) Date of Patent: *Nov. 12, 2024

(54) APPARATUS AND METHOD TO GUIDE ULTRASOUND ACQUISITION OF THE PERIPHERAL ARTERIES IN THE TRANSVERSE PLANE

(71) Applicant: Atherosys, Inc., Issaquah, WA (US)

(72) Inventors: Ram L. Bedi, Issaquah, WA (US); Todor Jeliaskov, Scottsdale, AZ (US); Charles D. Emery, Gilbert, AZ (US); Ivan S. Mitzev, Sofia (BG)

(73) Assignee: Atherosys, Inc., Issaquah, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/456,400

(22) Filed: Aug. 25, 2023

(65) Prior Publication Data

US 2023/0404523 A1 Dec. 21, 2023

Related U.S. Application Data

(63) Continuation of application No. 16/268,151, filed on Feb. 5, 2019, now Pat. No. 11,771,399.
(Continued)

(51) Int. Cl.
*A61B 8/08* (2006.01)
*A61B 5/00* (2006.01)
(Continued)

(52) U.S. Cl.
CPC .......... *A61B 8/0891* (2013.01); *A61B 5/7405* (2013.01); *A61B 5/742* (2013.01);
(Continued)

(58) Field of Classification Search
CPC ........ A61B 8/0891; A61B 8/488; A61B 5/489
See application file for complete search history.

(56) References Cited

U.S. PATENT DOCUMENTS

| 4,945,478 A | 7/1990 | Merickel et al. |
| 5,954,653 A | 9/1999 | Hatfield et al. |

(Continued)

FOREIGN PATENT DOCUMENTS

| CN | 106388867 A | 2/2017 |
| EP | 2163202 A1 | 3/2010 |

(Continued)

OTHER PUBLICATIONS

F. Molinari et al, "Automated carotid IMT measurement and its validation in low contrast ultrasound database of patient indian population epidemiological study: results of AtheroEdge™ Software", International Angiology, vol. 31, No. 1, pp. 1-22, Feb. 2012 (Year: 2012).*

(Continued)

*Primary Examiner* — Joel Lamprecht
*Assistant Examiner* — Nyrobi Celestine
(74) *Attorney, Agent, or Firm* — Perkins Coie LLP

(57) ABSTRACT

An ultrasound imaging system for guiding a user to acquire ultrasound image data sets that can be analyzed for the presence of atherosclerosis. In one embodiment, the processor is programmed to analyze ultrasound image data for a vessel of interest and to control a user interface that suggests how an operator should move a transducer to acquire ultrasound image data with the vessel of interest in a desired location. The processor stores multiple ultrasound image data sets taken along a length of the vessel of interest to be analyzed for the presence of an atheroma.

18 Claims, 23 Drawing Sheets

Related U.S. Application Data

(60) Provisional application No. 62/627,457, filed on Feb. 7, 2018.

(51) Int. Cl.
*A61B 8/00* (2006.01)
*A61B 8/06* (2006.01)
*A61B 8/14* (2006.01)

(52) U.S. Cl.
CPC .............. *A61B 5/7455* (2013.01); *A61B 8/06* (2013.01); *A61B 8/085* (2013.01); *A61B 8/14* (2013.01); *A61B 8/42* (2013.01); *A61B 8/4444* (2013.01); *A61B 8/4461* (2013.01); *A61B 8/463* (2013.01); *A61B 8/488* (2013.01); *A61B 8/5223* (2013.01); *A61B 8/5292* (2013.01); *A61B 8/0858* (2013.01)

(56) References Cited

U.S. PATENT DOCUMENTS

| | | |
|---|---|---|
| 6,023,968 A | 2/2000 | Spratt et al. |
| 6,139,496 A | 10/2000 | Chen et al. |
| 6,537,220 B1 | 3/2003 | Friemel et al. |
| 6,695,784 B1 | 2/2004 | Michaell |
| 7,356,367 B2 | 4/2008 | Liang et al. |
| 7,569,016 B2 | 8/2009 | Watanabe et al. |
| 7,925,064 B2 | 4/2011 | Cloutier et al. |
| 8,075,488 B2 | 12/2011 | Burton |
| 8,167,805 B2 | 5/2012 | Emery et al. |
| 8,491,484 B2 | 7/2013 | Lewis |
| 8,687,862 B2 | 4/2014 | Hsu et al. |
| 8,740,796 B2 | 6/2014 | Fukumoto et al. |
| 9,179,889 B2 | 11/2015 | Fukumoto et al. |
| 9,192,352 B2 | 11/2015 | Yao et al. |
| 9,220,477 B2 | 12/2015 | Urabe et al. |
| 9,357,980 B2 | 6/2016 | Toji et al. |
| 9,498,185 B2 | 11/2016 | Kimoto et al. |
| 9,693,755 B2 | 7/2017 | Kondoh |
| 9,770,227 B2 | 9/2017 | Kawabata et al. |
| 10,722,209 B2 | 7/2020 | Chen et al. |
| 2004/0116813 A1 | 6/2004 | Selzer et al. |
| 2005/0096528 A1 | 5/2005 | Fritz et al. |
| 2005/0182319 A1 | 8/2005 | Glossop |
| 2008/0070915 A1 | 3/2008 | Guillemont et al. |
| 2008/0171939 A1 | 7/2008 | Ishihara |
| 2009/0105579 A1 | 4/2009 | Garibaldi |
| 2009/0275834 A1 | 11/2009 | Watanabe et al. |
| 2009/0306509 A1 | 12/2009 | Pedersen et al. |
| 2010/0113930 A1 | 5/2010 | Miyachi |
| 2010/0210946 A1 | 8/2010 | Harada et al. |
| 2010/0240992 A1 | 9/2010 | Hao |
| 2011/0257527 A1 | 10/2011 | Suri |
| 2011/0299754 A1 | 12/2011 | Suri |
| 2012/0078099 A1 | 3/2012 | Suri |
| 2012/0179042 A1 | 7/2012 | Fukumoto et al. |
| 2012/0296214 A1 | 11/2012 | Urabe et al. |
| 2013/0046168 A1 | 2/2013 | Sui |
| 2013/0218024 A1 | 8/2013 | Boctor et al. |
| 2013/0321262 A1 | 12/2013 | Schecter |
| 2014/0066770 A1 | 3/2014 | Watanabe et al. |
| 2014/0081142 A1 | 3/2014 | Toma et al. |
| 2014/0100440 A1 | 4/2014 | Cheline et al. |
| 2014/0249417 A1 | 9/2014 | Ookouchi et al. |
| 2014/0275986 A1 | 9/2014 | Vertikov |
| 2014/0276059 A1 | 9/2014 | Sheehan |
| 2014/0276062 A1 | 9/2014 | Kondoh |
| 2014/0303499 A1* | 10/2014 | Toma ..................... G16H 50/30 600/454 |
| 2014/0369583 A1 | 12/2014 | Toji et al. |
| 2014/0371593 A1 | 12/2014 | Kondoh |
| 2015/0009997 A1 | 1/2015 | Balassanian |
| 2015/0055846 A1 | 2/2015 | Haque |
| 2015/0025380 A1 | 6/2015 | Azegami et al. |
| 2015/0209004 A1 | 6/2015 | Tamada |
| 2015/0310581 A1 | 10/2015 | Radulescu et al. |
| 2015/0359512 A1 | 12/2015 | Boctor et al. |
| 2015/0359605 A1 | 12/2015 | O'Brien-Coon et al. |
| 2016/0000408 A1 | 1/2016 | Matsunaga et al. |
| 2016/0157814 A1 | 6/2016 | Palanisamy et al. |
| 2016/0157826 A1 | 6/2016 | Sisodia et al. |
| 2016/0331469 A1 | 11/2016 | Hall et al. |
| 2016/0374562 A1 | 12/2016 | Vertikov |
| 2017/0032995 A1 | 2/2017 | Cox |
| 2017/0090571 A1 | 3/2017 | Bjaerum et al. |
| 2017/0265831 A1 | 9/2017 | Sankaran et al. |
| 2017/0372475 A1 | 12/2017 | Gulsun et al. |
| 2018/0014810 A1 | 1/2018 | Chen et al. |
| 2018/0220991 A1 | 8/2018 | O'Brien et al. |
| 2019/0015078 A1 | 1/2019 | Saad et al. |
| 2019/0046153 A1 | 2/2019 | Tanaka et al. |
| 2019/0239848 A1 | 8/2019 | Bedi et al. |
| 2020/0151872 A1 | 5/2020 | Ma et al. |

FOREIGN PATENT DOCUMENTS

| | | |
|---|---|---|
| EP | 1997436 B1 | 10/2014 |
| JP | 2008161220 A | 7/2008 |
| KR | 1020140103932 | 8/2014 |
| WO | 2013067419 A1 | 5/2013 |
| WO | 2019212992 | 11/2019 |

OTHER PUBLICATIONS

R. Menchon-Lara et al, "Automatic detection of the intima-media thickness in ultrasound images of the common carotid artery using neural networks", Medicine & Biological Engineering & Computing, vol. 52, pp. 169-181, Nov. 2013 (Year: 2013).*

R. Menchon-Lara et al, "Early-stage atherosclerosis detection using deep learning over carotid ultrasound images", Applied Soft Computing, vol. 49, pp. 616-628, Sep. 2016 (Year: 2016).*

F. Faita et al, "Real-time Measurement System for Evaluation of the Carotid Intima-Media Thickness With a Robust Edge Operator", Journal of Ultrasound Medicine, vol. 27, p. 1353-1361, 2008 (Year: 2008).*

Akosha, et al., "Carotid ultrasound for risk clarification in young to middle-aged adults undergoing elective coronary angiography," Am J. Hypertens 19(12):1256-61, Dec. 2006.

Akosha, et al., "Pilot results of the Early Detection by Ultrasound of Carotid Artery Intima-Media Thickness Evaluation (EDUCATE) study," Am. J. Hypertens 20:1183-1188, Nov. 2007.

Camacho, et al., "Phase Coherence Imaging," IEEE Transactions on Ultrasonics, Ferroelectrics, and Frequency Control, vol. 56, No. 5, pp. 958-974, May 2009.

Canny, J., "A Computational Approach to Edge Detection," IEEE Trans. Pattern Anal. Mach. Intell., Jun. 1986;8(6):679-98.

Demi, et al., "The first order absolute moment in low-level image processing," in Proceedings of 13th International Conference on Digital Signal Processing, vol. 2, No. 1, pp. 511-514, 1997.

Drechsler, et al., "Hierarchical decomposition of vessel skeletons for graph creation and feature extraction," Proc.—2010 IEEE Int. Conf. on Bioinformatics and Biomedicine BIBM 2010, pp. 456-461, 2010.

Ibanez, et al., "Diagnosis of Atherosclerosis by Imaging," The American Journal of Medicine, vol. 122, Issue 1, Supplement, Jan. 2009, pap. S15-S25.

Illea, et al., "Fully Automated Segmentation and Tracking of the Intima Media Thickness in Ultrasound Video Sequences of the Common Carotid Artery," IEEE Trans. Ultrason. Ferroelectr. Freq. Control, vol. 60, No. 1, pp. 158-177, Jan. 2013.

Jespersen, et al., "Multi-Angle Compound Imaging," Ultrasonic Imaging, 20(2):81-102, May 1998.

Li, et al., "Adaptive Imaging Using the Generalized Coherence Factor," IEEE Transactions on Ultrasonics, Ferroelectrics and Frequency Control, vol. 50, No. 2, pp. 128-141, 2003.

Lorenz, et al., "A Guassian model approach for the prediction of speckle reduction with spatial and frequency compounding," Proceedings of the IEEE Ultrasonics Symposium 2:1097-1101 vol. 2, Dec. 1996.

(56) References Cited

OTHER PUBLICATIONS

Mitzev, et al., "Concatenated decision paths classification for datasets with small number of class labels," ICPRAM 2017, Porto, Portugal, Feb. 2017, pp. 410-417.
Molinari, et al., "A state of the art review on intima-media thickness (IMT) measurement and wall segmentation techniques for carotid ultrasound," Comput. Methods Programs Biomed., vol. 100, No. 3, pp. 201-221, 2010.
Neuschler, et al., "Diagnosis of Breast Masses Using Opto-Acoustics," American Roentgen Ray Society, MS Powerpoint Presentation, pp. 1-40.
Oraevsky, A. A., Optoacoustic tomography of the breast, Chapter 33 in "Photoacoustic imaging and spectroscopy," ed. By L. Wang, Taylor and Francis Group, New York, 2009.
Otsu, N., "A Threshold Selection Method from Gray-Level Histograms," IEEE Trans. Sys. Man. Cyber, vol. SMC-9, No. 1, pp. 62-66, 1979.
Rossi, et al., "Automatic localization of intimal and adventitial carotid artery layers with noninvasive ultrasound: a novel of algorithm providing scan quality control," Ultrasound Med. Biol., vol. 36, No. 3, pp. 467-479, Mar. 2010.
Touboul, et al., "Mannheim Carotid Intima-Media Thickness Consensus (2004-2006)," Cardiovascular Diseases, vol. 23, pp. 75-80, 2007.
International Searching Authority, International Search Report and Written Opinion of PCT/US2019/016663 mailed Apr. 24, 2019, 10 pages.
Best, S., "The Future of Medical Scans? Nintendo Wi-inspired 7 Pound Microchip Turns 2D Ultrasound Machines into 3D Imaging Devices,", DailyMail.com, Oct. 31, 2017, http://www.dailymail.co.uk/sciencetech/article-5035775/Microchip-turns-ultrasound-machines-3D-image-devices.html.
U.S. Appl. No. 62/627,457, filed Feb. 7, 2018.
Hasegawa, H., et al., "Detection of lumen-intima interface of posterior wall for measurement of eslasticity of the humad carotid artery," IEEE Transactions on Ultrasonic, Ferroelectrics, and Frequency Control, IEEE, USA, col. 51, No. 1, pp. 93-108.
Eigenbroft, M. L. et al., "B-mode ultrasound common carotid artery intima-media thickness and external diameter: cross-sectional and longitudinal associations with carotid atherosclerosis in a large population sample," Cardiovascular Ultrasound, vol. 6, Mar. 5, 2008.
International Searching Authority, International Search Report and Written Opinion of PCT/US2019/016663, mailed Jul. 8, 2019; 13 pages.
Communication pursuant to Article 94(3) EPC mailed Jan. 31, 2024 for European Patent Application No. 19750807.0.
Eigenbrodt, M. et al., "B-mode ultrasound common carotid artery intima-media thickness and external diameter: Cross-sectional and longitudinal associations with carotid atherosclerosis in a large population sample," Cardiovascular Ultrasound, vol. 6, 2008.
Extended European Search Report mailed Jan. 4, 2022 for European Patent Application No. 19796479.4.
Hasegawa, Hideyuki, et al., "Detection of Lumen-Intima Interface of Posterior Wall for Measurement of Elasticity of the Human Carotid Artery," IEEE Transactions on Ultrasonics, Ferroelectrics, and Frequency Control, vol. 51, No. 1, pp. 93-108, 2004.
International Search Report and Written Opinion mailed Jul. 8, 2019 for International Patent Application No. PCT/US19/29739.
Li, Pai-Chi and Li, Meng-Lin, "Adaptive Imaging Using the Generalized Coherence Factor", IEEE Transactions on Ultrasonics, Ferroelectrics and Frequency Control, vol. 50, No. 2, pp. 128-141.

\* cited by examiner

APPARATUS AND METHOD TO GUIDE ULTRASOUND ACQUISITION OF THE PERIPHERAL ARTERIES IN THE TRANSVERSE PLANE

CROSS-REFERENCE TO RELATED APPLICATION(S)

The present application is a continuation of U.S. Non-Provisional patent application Ser. No. 16/268,151 filed Feb. 5, 2019, which claims the benefit of, and priority to, U.S. Provisional Patent Application No. 62/627,457 filed Feb. 7, 2018, the disclosures of which are incorporated herein by reference in their entireties.

TECHNICAL FIELD

This invention relates to an apparatus and method for the automatic detection of incipient atheroma in the asymptomatic population, which is important in preventative medicine. The elegance of the apparatus and method described is in the simplicity of acquiring, optimizing, analyzing, and calculating whether an asymptomatic individual should receive cholesterol lowering drugs or other medical therapies. Specifically, this invention refers to a new diagnostic ultrasound apparatus and method which enables primary care physicians to detect the presence of atherosclerosis so they can better target individuals who would benefit from preventive medical interventions.

BACKGROUND

Diagnostic ultrasound is routinely used in a hospital setting worldwide. However, its core advantages of non-ionizing radiation, low cost and portability are not exploited in the much larger and more frequently utilized primary care market. While perceived impediments of size, weight and cost have been addressed by incumbent developers, the real impediment to widespread adoption in a primary care setting is the prohibitive overhead cost of acquisition expertise by a sonographer and interpretation aptitude by a radiologist. This invention aims to remedy this hurdle by focusing on a specific disease which affects a significant percentage of the population and by automating many of the steps for image acquisition and interpretation.

The invention targets the detection of subclinical atherosclerotic cardiovascular disease (ASCVD), which is a chronic disorder developing insidiously throughout life and eventually manifesting itself into catastrophic symptoms of myocardial infarction and ischemic stroke. Per the World Health Organization (WHO), 17.5 million people worldwide and 800,000 in the USA died from cardiovascular diseases in 2005; with the worldwide number expected to increase to almost 25 million by 2020. Most of these deaths could be prevented or delayed through judicious choice of lifestyle modifications and initiation of lipid lowering therapy. The decision to offer medical intervention to select individuals based solely on risk factor assessment is not adequate.

This invention aims to provide physicians with direct evidence of progression to arterial damage from ASCVD risk factors so they can more aggressively target such individuals with lipid lowering therapy.

As mentioned earlier, a key component to increase the adoption of ultrasound imaging in the primary care physician's office is simplification of the apparatus and methods used to successfully acquire ultrasound images of peripheral arteries such as the extracranial carotid, brachial, iliac and femoral arteries. The acquired images can then be automatically analyzed to determine the patient's suitability for medical intervention. The following disclosure describes the apparatus and method that may be used to effectively acquire real-time ultrasound images for an entire volume which can be used for further detailed analysis to guide the decision for medical intervention.

SUMMARY

As will be discussed in detail below, the disclosed technology relates to an ultrasound imaging system that is configured to guide a user in creating a number of ultrasound image data sets from which an assessment of atherosclerosis can be determined by computer. In some embodiments, a processor is programmed to analyze image data sets and produce feedback for the user to capture images that are perpendicular or nearly perpendicular to fluid flow in a vessel. The user is directed by the processor to capture sequential images along a length of a vessel to capture image data sets that are used to estimate volumes of atherosclerotic tissue.

DETAILED DESCRIPTION

Disease Description and Key Health Indicator

The extracranial carotid and femoral arteries are key vascular areas where physicians look for the development of potential atherosclerotic plaques since disease found in these regions suggests atherosclerotic plaques may be forming in other arteries. Although the following description focuses on the carotid, it is important to note that these same techniques can be utilized for other peripheral arteries such as the iliac, femoral and brachial where anatomical features define the start and the stop of the ultrasound scan.

Figure 1A:
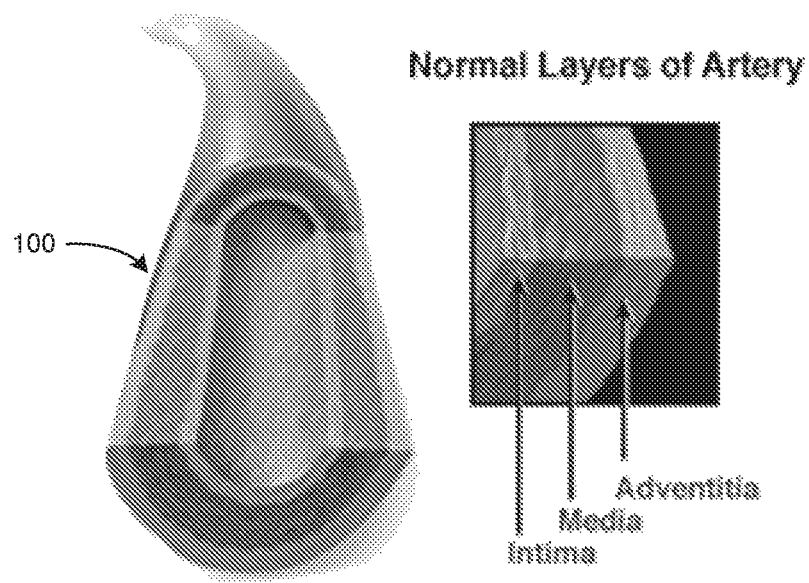
FIGS. 1a and 1b illustrate a normal artery cross section and an artery with atheroma.
Figure 1B:
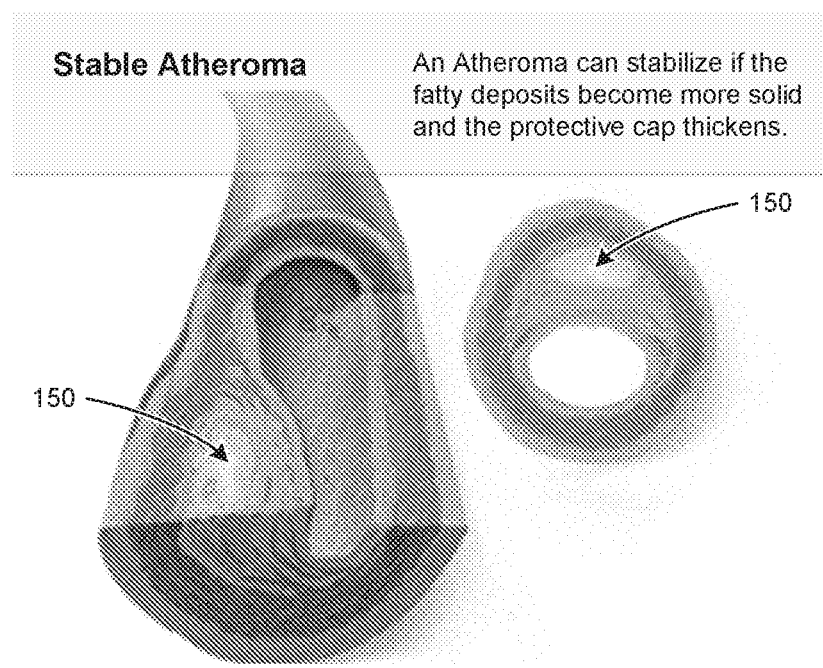

FIG. 1a shows a three-dimensional (3D) sketch of a healthy carotid wall 100 which consists of adventitia, media, and intima. FIG. 1b shows a case where an atheromatous plaque 150 has started to build up in the arterial wall which creates less optimal flow. Ultrasound B-mode imaging is the preferred method of determining arterial health noninvasively. Assessment of the atheroma using ultrasound is optimal when cross-sectional images of the artery are acquired with the imaging plane nearly perpendicular to the wall for optimal contrast.

Ultrasound Acquisition Methods

Since the presence of an atheroma is a key characteristic of arterial health, acquiring images of the carotid with optimal spatial and temporal resolution and contrast will yield a better diagnosis. This is accomplished by:

Setting the azimuth transmit focal depth as close to the lumen center of the carotid Keeping the carotid in the middle of the ultrasound acquisition plane which yields optimal lateral resolution Maintaining the imaging plane such that it is approximately orthogonal to the carotid longitudinal axis (transverse plane)

Obtaining channel data for application of methods to improve lumen and wall contrast during post processing and analysis (see the cites to Li, Pai-Chi and Camacho, Jorge cites below)

Maximizing of possible compound angles to enhance wall edge contrast to the lumen By keeping the carotid in the middle (or nearly the middle e.g. +/−0 to 20% from a center point) of the ultrasound image, maximum contrast and spatial resolution is achieved in the vessel of interest (VOI) since the full extent of the transducer aperture may be used. In a high frequency linear array, which is the recommended aperture design to acquire B-mode images, penetration as well as detail and axial resolution tend to decrease near the edges of the array since the aperture width for the acquired vector is smaller.

While keeping the carotid cross-section in the middle of the B-mode image, unique 3D virtual apertures may also be created to enable multiple look angles at the vessel which may enhance detection of the arterial wall without a frame rate impact. Virtual apertures also offer many other advantages such as:

Variety of look angles—Off-line processing enables multiple steering angles to the vessel wall based on segmentation which optimizes contrast Variety of focal depths—The variety of look angles optimizes the contrast between the vessel wall and lumen; however, placing the focus at the wall or inside the lumen can further enhance this brightness difference Maximization of frame rates—Virtual apertures typically only require one transmit focus and one receive focus per vector which minimizes acquisition time. Conventional techniques incorporate all necessary steering angles and transmit foci prior to acquisition even though this may not be ideal. The more steering angles, the greater the reduction in frame rate.

Computation minimization—VOI adjusts real-time to follow the carotid which limits the number of ultrasound vectors since the image only needs to include the carotid Virtual volume imaging—2D array apertures may be generated for volume imaging by expanding the virtual elements in three dimensions.

If the carotid moves to either edge of the imaging window, then optimal pairs of transmit and receive beams that are approximately orthogonal to the entire vessel perimeter may not be available. This diminishes the ability to optimally detect the arterial wall and acquire the necessary images for diagnostic purposes. As the carotid gets closer to the imaging plane edge, the advantage of the virtual aperture diminishes.

Since the goal is to keep the carotid in approximately the middle of the B-mode image such that optimal resolution is achieved (e.g. uses the largest possible aperture), then real-time feedback based on the acquired ultrasound images and data of the carotid guides the user during the manual acquisition. The transducer orientation guide section below describes some of these methods such as which way to translate, tip, and tilt the transducer. In one case, the orientation guide includes feedback as to if the acquired data meets certain criteria such as wall brightness, contrast between the lumen and wall, and location of the carotid.

Some of the key acquisition methods listed above are typically performed manually by a sonographer or radiologist since they are trained to adjust system settings to obtain the necessary B-mode data. Since this apparatus is expected to be placed in the office of a primary care physician, the disclosed technology is programmed to simplify and automate the acquisition process to minimize the amount of ultrasound expertise required to obtain the necessary data for the diagnosis. These features enable the adoption of this technology in a primary care physician office.

Semi-Automated Acquisition for PCPs

Figure 2:
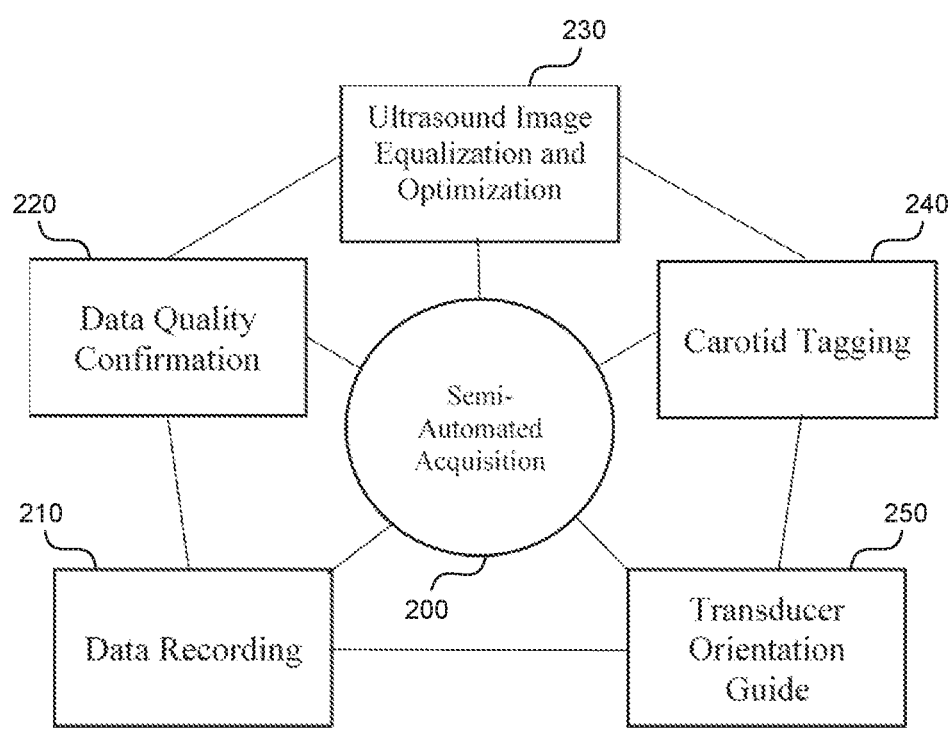
FIG. 2 illustrates functional components of an atheroma detection system in accordance with some embodiments of the disclosed technology.

The process steps for acquiring spatially registered B-mode ultrasound images are shown in FIG. 2. The blocks of steps may be used simultaneously during the acquisition. In one embodiment, the blocks include a semi-automated data acquisition block 200, a data recording block, 210, a data quality confirmation block, 220, an ultrasound image and equalization block 230, a carotid tagging block 240 and a transducer orientation guide block 250.

Ultrasound Image Equalization and Optimization

Starting with the ultrasound image equalization and optimization block 230 shown in FIG. 2, it is assumed that the user performing the study has sufficient knowledge of anatomy and the approximate location of the carotid. Furthermore, remote palpation or a heart rate monitor may be used to obtain a general location of the carotid prior to starting the study which is directly above the clavicle. The study begins by placing the dedicated transducer on the approximate location of the carotid.

In this step, the transducer is placed such that the imaging plane sits mostly along the longitudinal axis of the carotid rather than the transverse axis. This is entirely acceptable at this stage since the processor of the system is programmed to acquire initial backscatter characteristics from the vessel of interest to properly set specific acquisition parameters such as transmit frequency and bandwidth, receive gain and bandwidth, and dynamic range for the pending acquisition. Ideally, the transducer is held in this fixed position until automatic assessment of the image is complete. Although this process is initially done prior to the acquisition, it is important to note that ultrasound image optimization may be implemented while the acquisition occurs. The system is configured to continuously and automatically set optimal transmit and receive parameters such as frequency, bandwidth, focus, gain, depth, steering angle, and dynamic range by analyzing the position of the identified vessel in one or more B-mode images and surrounding tissues, to allow precise optimal tracking of vessel of interest. It is not expected that the vessel will remain at the same depth through the scan and the surrounding tissue is like to change characteristics which requires parameter adjustment. After the tissue equalization and optimization is obtained through a computational assessment of the backscatter, the next step is to identify the carotid.

Carotid Tagging

The carotid tagging block 240 shown in FIG. 2 is implemented by the processor to locate the carotid (or other vessel of interest) in the ultrasound image data. First, the processor of the system is programmed to determine, based on the initial transducer placement, whether the B-mode image contains the carotid. Initial identification of the carotid is accomplished using one or more of the following criteria:

Brightness of the arterial wall

Darkness in the lumen

Brightness difference between the wall and lumen

Arterial wall pulsatility

Artery diameter

Distance between the distal and proximal walls

Presence of flow, (flowing towards the brain)

Incompressibility of the artery

Distance between the proximal and distal walls of the artery

Temporal changes in the blood throughout the cardiac cycle

Elastic properties of the vessel

Neural network training

Through a prior scan which successfully identified the artery

The carotid tagging occurs once enough of the criteria listed above are satisfied with a specific level of confidence. The tagging allows the system to set any brightness level filters which may consist of a notch filter to enhance the lumen and arterial wall.

As the data is acquired, the incoming ultrasound images are processed to look for the key features previously listed. One key feature in identifying the carotid is a specular reflector (the artery wall) next to a dark region (lumen). The strength of the specular reflector is the strongest when the ultrasound vector is perpendicular to the arterial wall. Therefore, to identify the carotid, the acquired images which are at different steering angles are compared against an expected feature geometry. If a similar specular reflector is detected at the same steering angle within an acceptable separation distance, then the identified object may be considered the carotid with a specific confidence level. The identified object is assessed for other key carotid features such as pulsatility and distance or diameter between the specular reflectors which may also be used to increase the confidence. The pulsatility is determined by monitoring the wall motion which was identified as a specular reflector. The minimum distance between the identified specular reflectors at the same steering angle is determined through edge detection methods. Compressibility is determined by having the operator apply a remote force which further increases the confidence the carotid has been identified.

Although it is expected that the above list is sufficient, there are other means to identify the carotid. First, machine learning (ML) may be employed either using 2D or 3D data sets since it is unknown the transducer orientation relative to the carotid. Another means of identification is through 2D or 3D image correlation to a prior study of the same patient. Finally, the carotid may also be simply obtained through nurse and physician training which could may accomplished through a touch screen which acts to seed the algorithm so carotid tracking is accomplished through the entire registered volume scan.

Carotid tagging identifies the vessel in the image to be tracked and enables the movement of this technique into the primary care physician's office. The following section gives additional details on the process of carotid tagging.

Carotid Taging: Detailed Description

Figure 3:
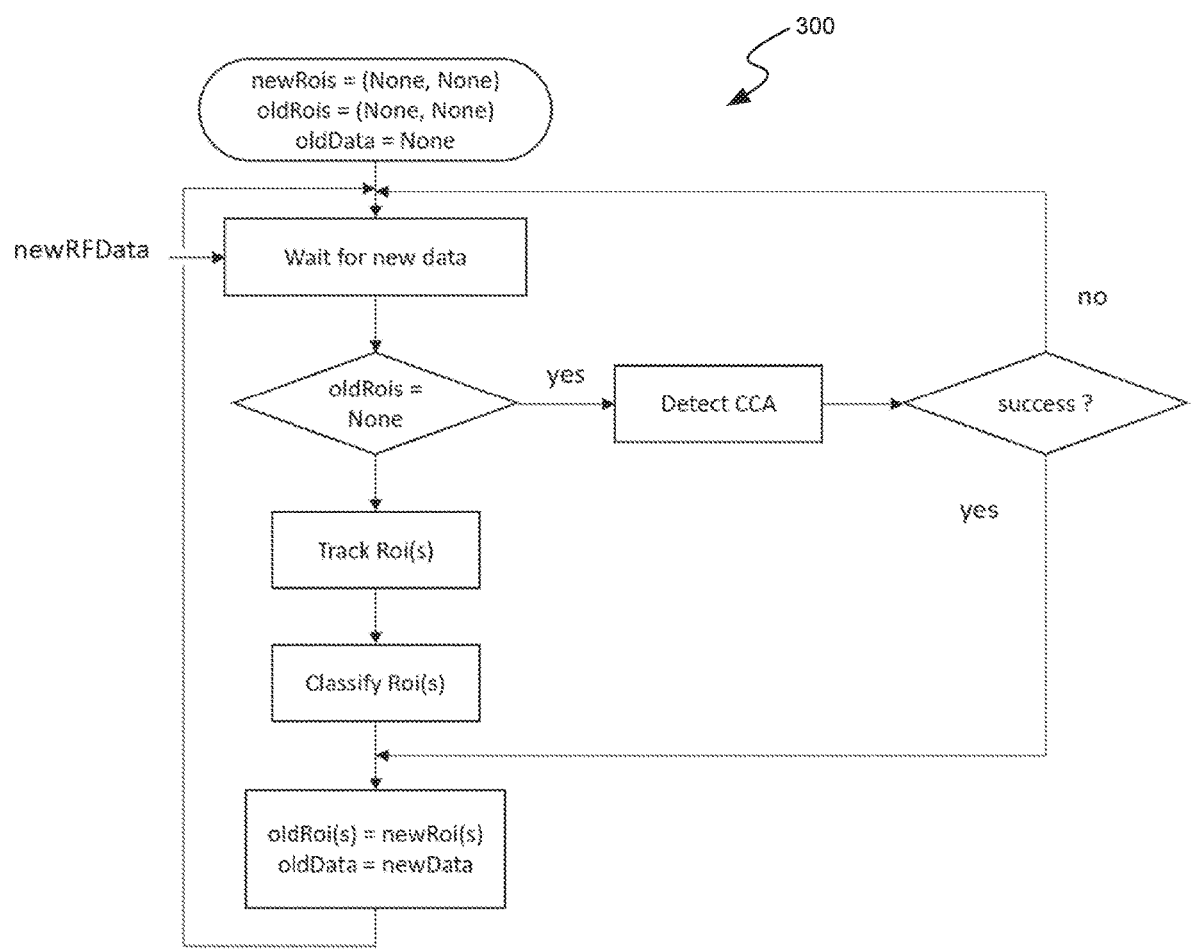
FIG. 3 is a flow diagram of steps performed by a programmed processor or configured logic to detect a carotid in a subject in accordance with some embodiments of the disclosed technology.

The Carotid Tagging Block 240 is responsible for the detection of the presence of carotid and for the identification of its span (vessel of interest). The flow chart 300 of the operations performed by one or more programmed processors, DSP, ASICs or other configured logic circuitry are shown in FIG. 3. During main operation, the block waits for the reception of new frame of data. If an initial vessel of interest (VOI) has been identified, then the VOI is tracked to the new frame using block or pattern matching. The carotid tagging block can track 1 (one) or 2 (two) vessels of interest. After the new position of the VOI is identified, the data supporting the VOI is segmented, and the VOI is either kept as a single VOI in the case of common carotid artery, or the VOI is split into two after the bifurcation of the carotid artery (interior and exterior carotid arteries). Finally, the reference data for tracking is updated, and the block waits for the reception of the next data set.

Figure 4B:
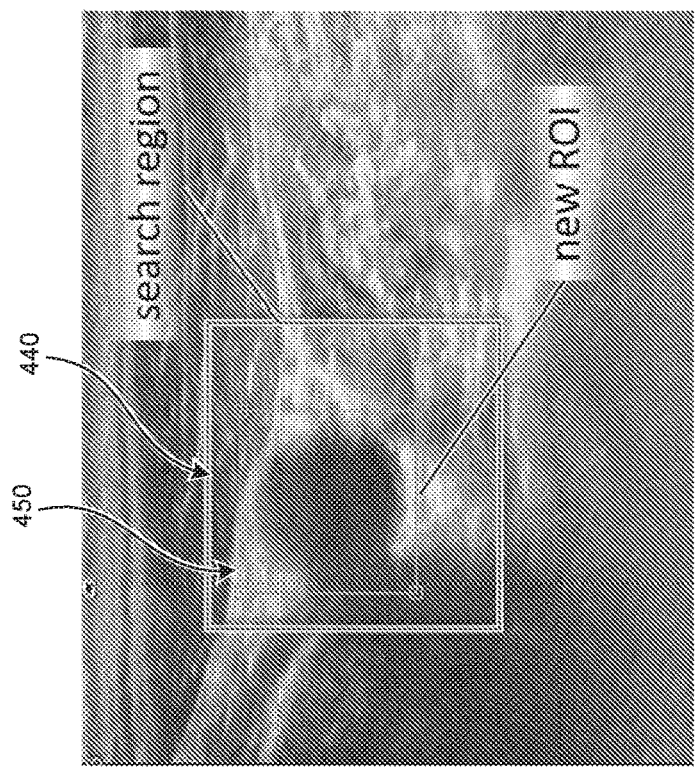
FIGS. 4a and 4b illustrate the refinement of a region of interest in a search region in an ultrasound dataset to locate a carotid.
Figure 4A:
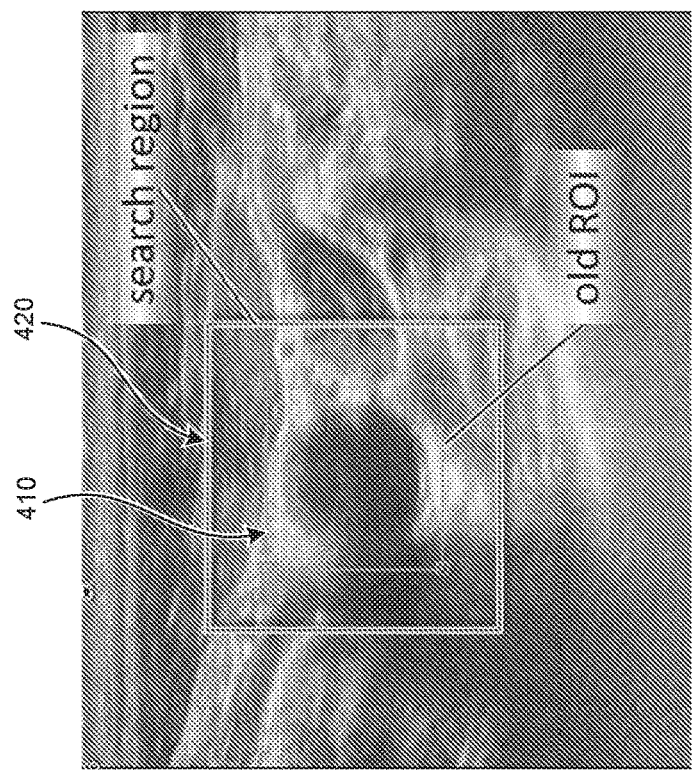

The tracking of the vessel of interest is performed using block matching as shown in FIGS. 4(*a*) and 4(*b*), which is an example of how VOI is tracked between adjacent frames using a block matching algorithm. The left sub-FIG. 4*a* shows the old frame of data, the identified vessel of interest 410 for the common carotid artery and a search region 420 including the vessel of interest. The right sub-FIG. 4*b* shows the "new" frame of data (closer to the bifurcation), a search region 440 (identical to the search region 420 shown in the left sub-FIG. 4*a*), and the new VOI 450. The new VOI 450 is identified as the part of the image which matches best the part of the image from the old vessel of interest 410. This process may occur at any location along the common carotid.

Any block matching algorithm can be used to track the vessel of interest between two pairs of data frames, such as the position of the minimum of the sum of squared differences, or the position of the minimum of the sum of absolute differences, or the position of the maximum of the normalized cross-correlation function. These are standard block matching algorithms used for motion estimation and tracking see A Kaehler and G. Bradski, Learning OpenCV 3: Computer Vision in C++ with the OpenCV Library, O'Reilly Media, Inc. 2016.

In one embodiment, successful tracking of the position of the carotid artery through the volume is accomplished by adjusting of the size of VOI for every frame, after detection of the translation between the two frames which helps limit the amount of data to acquire and the time required for each acquisition.

Figure 7:
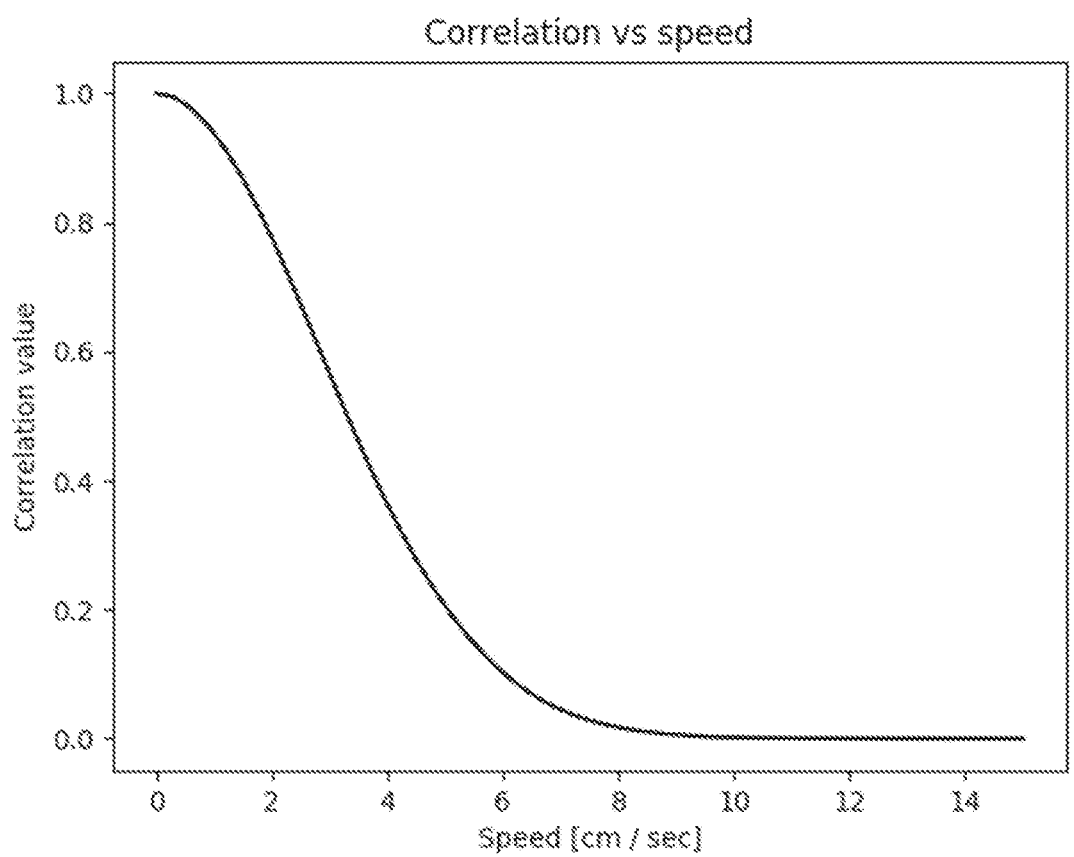
FIG. 7 illustrates correlation value versus the speed of blood of an artery. The assumption is that the scan is performed in a plane orthogonal to the flow direction i.e. the blood enters and exits the scan plane. The values for the correlation are calculated assuming that the bean profiles in elevation direction are Gaussian-shaped, with full width at half maximum (FWHM) $\lambda \cdot f_n$, where $\lambda$ is the wavelength of the ultrasound pulse and $f_n$ is the focusing strength. The transducer is assumed to have a center frequency of 10 MHz. The speed of sound is assumed to be 1540 m/s. The focus number $f_n$ is set to 5.5, which is a typical value for imaging the transducer. The PRF is 15 kHz and the number of lines is 192 giving a frame rate of 78 Hz.

If an initial VOI has not been identified yet, then an initial VOI is identified by the Detect CCA block shown in FIG. 7 which shows the correlation value vs the speed of blood. The assumption is that the scan is performed in a plane orthogonal to the flow direction, i.e. the blood enters and exits the scan plane. The values for the correlation are calculated assuming that the beam profile in elevation direction is Gaussian-shaped, with full width at half maximum (FWHM) of $\lambda \cdot f\_\#$, where $\lambda$ is the wavelength of the ultrasound pulse, and $f\_\#$ is the focusing strength. The transducer is assumed to have a center frequency of 10 MHz. The speed of sound is assumed to be 1540 m/s. The focus number, $f\_\#$, is set to 5.5, which is a typical value for imaging transducers. The PRF is 15 kHz, and the number of lines in the image is 192 giving a frame rate of 78 Hz. Details for the correlation as a function of lateral displacement/motion are "common knowledge."

Figure 9:
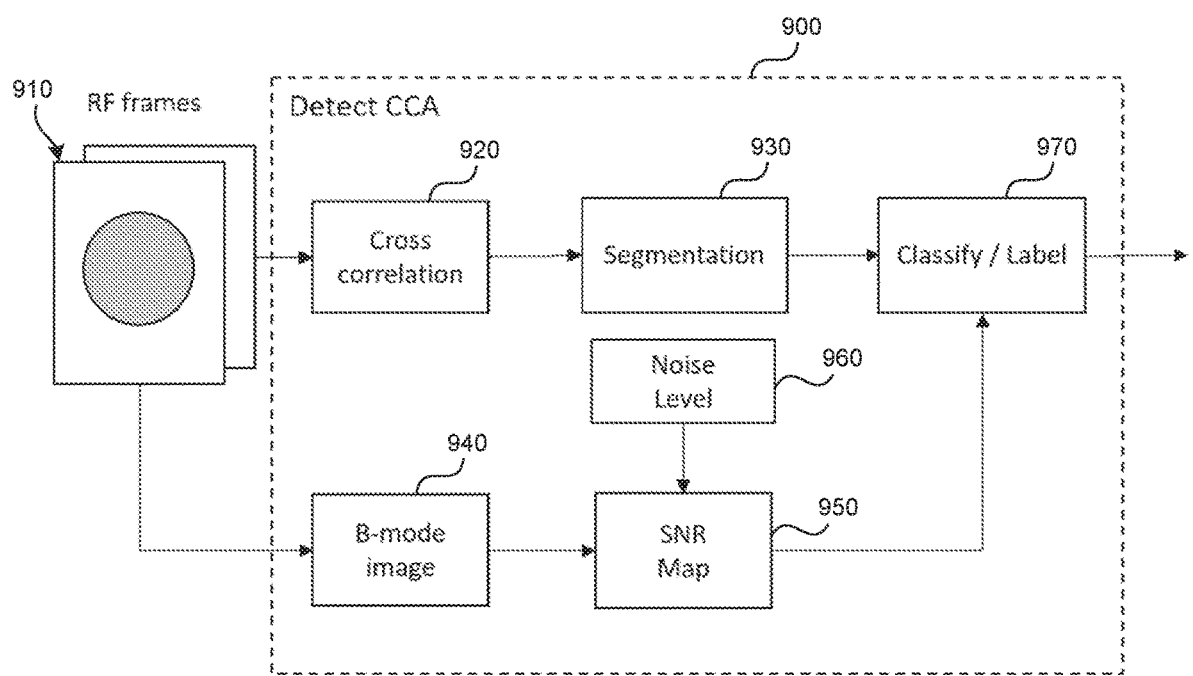
FIG. 9 shows a system for detecting the common carotid in accordance with some embodiments of the disclosed technology. The detection of the common carotid is based on correlation of sequential frames. A sequence of RF frames (2 or more) are fed in a block that estimates a normalized cross-correlation for each frame. The cross-correlation is segmented. The segmentation threshold is chosen based on the a priori knowledge about the correlation of blood. The RF frames are also fed to a module that generates B-mode images. The pixel level of the B-mode image is used to create a map of the signal to noise ratio (SNR) map. The map level of the (thermal) noise is tabulated per setup during the production of the device. The SNR Map and the segmented cross-correlation are then fed to a block that labels the regions to the image. Only one continuous region is classified and labeled as being the common carotid (CCA).

Different methods can be used to identify initially the common carotid artery: acquire color flow map simultaneously with a B-mode image, machine learning and computer vision algorithms to detect the carotid artery, etc. A preferred embodiment is to use a combination of frame to frame correlation, augmented by a signal-to-noise estimator and a classifier using machine learning. The Detect CCA block 900 in FIG. 9 uses as a main input correlation between sequential planes, and the fact that (1) signals decorrelate faster with larger motion, (2) that the signal-to-noise ratio can be used to discriminate between blood echoes, which have low correlation, and noise-dominated echoes which also have low correlation. FIG. 9 shows the block that performs the initial detection of the common carotid artery. The detection of the common carotid artery is based on correlation of sequential frames. A sequence of RF frames 910 (2 or more) are fed in a block 920 that estimates a normalized cross-correlation from each frame. The cross-correlation map is segmented at block 930. The segmentation threshold is chosen based on the a priori knowledge about correlation of blood. The RF frames are also fed to a module 940 that generates B-mode images. The pixel level of the B-mode image is used to create a map of the signal-to-noise ratio (SNR Map) at block 950. The map level of the (thermal) noise 960 is tabulated per setup during the production of the device. The SNR Map and the segmented cross-correlation are then fed to a block 970 that labels the regions in the image. Only one continuous region is classified and labeled as being the common carotid artery (CCA).

Figure 5:
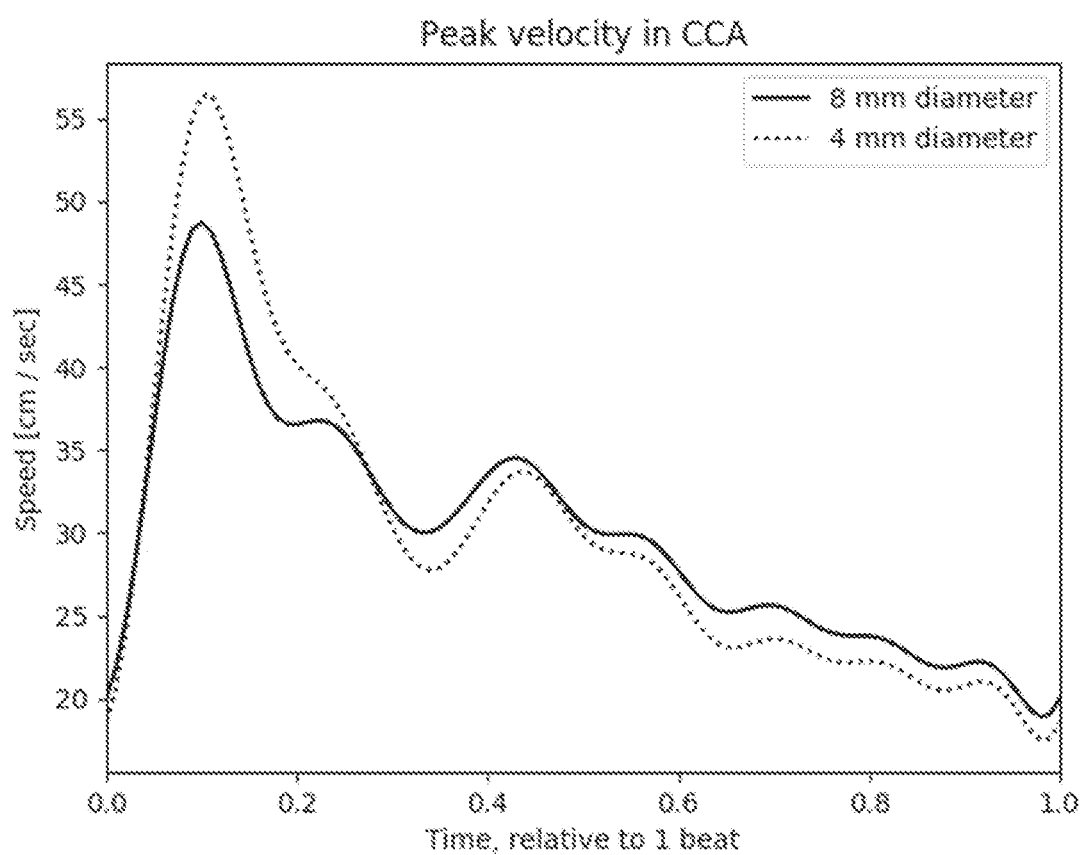
FIG. 5 illustrates peak velocity for ideal vessels with velocity profiles modelling the flow in the common carotid. The diameter of the typical carotid may vary between 4 and 8 mm. The velocities are calculated for vessels without or with minimum stenosis. The flow is assumed laminar with parabolic profile. In a typical vessel, the peak systolic velocity is above 40 cm/sec. The end diastolic velocity, in the middle of the vessel is about 20 cm/sec.
Figure 6:
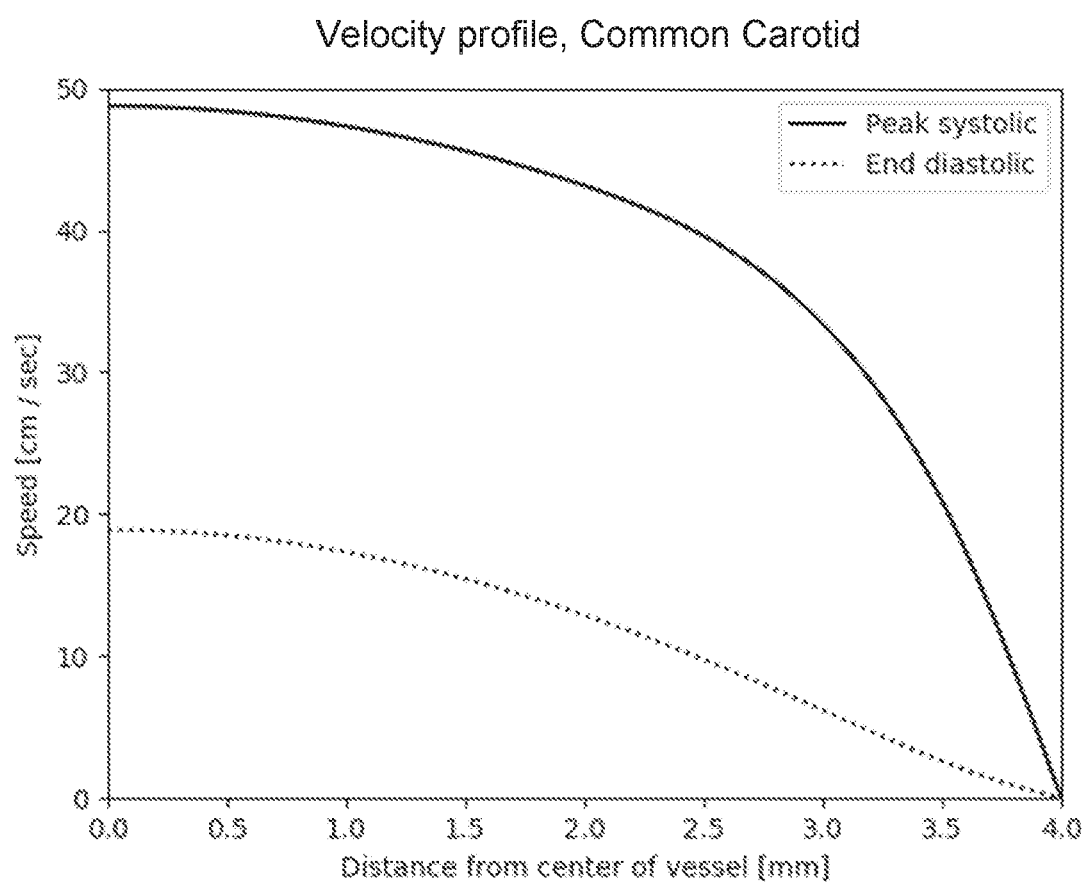
FIG. 6 illustrates blood velocity as a function of radial distance to the center of the vessel. Two profiles are shown: (1) peak systolic velocity and (2) end diastolic velocity. The velocity of the blood for the bigger portion of the vessel is larger than the velocity of the tissue, which is typically below 10 cm/sec.

The acquisition is performed by translating the probe along the carotid artery. The translation velocity is about 1 cm/s. The peak systolic velocity of the blood in the carotid artery is usually more than 40 cm/s and the end diastolic velocity is typically above 10 cm/s as shown in FIG. 5. FIG. 5 shows the velocity at the center of the common carotid artery as a function of time within a single heartbeat. There is a clear difference in velocity of the flowing blood, and the velocity of the tissue. FIG. 5 shows peak velocity for ideal vessels with velocity profiles modelling the flow in the common carotid artery. The diameters of typical carotid arteries may vary between 4 and 8 mm. The velocities are calculated for vessels without or with minimum stenosis. The flow is assumed laminar with parabolic profile. In a typical vessel, the peak systolic velocity is above 40 cm/sec. The end diastolic velocity, in the middle of the vessel is about 20 cm/sec. The parameters for the calculation are taken from Jensen 1995. FIG. 6 shows the blood velocity as a function of radial distance to the center of the vessel. Two profiles are shown: (1) peak systolic velocity and (2) end diastolic velocity. The velocity of the blood for the bigger portion of the vessel is larger than velocity of the tissue which typically below 10 cm/sec. FIG. 6 illustrates the profile of the blood speed as function of radial direction. 98% of blood moves faster than the tissue motion at peak of the systole, and 88% of the blood moves faster than the tissue.

The blood flows in a direction that is oblique, ideally perpendicular, to the imaging plane of the transducer. The beam of the transducer has some finite dimensions. A typical imaging transducer has elements which are between 20 and 25 wavelengths high, and are focused with an acoustic lens in elevation direction. The focusing number of the elevation focus is as a rule of thumb between 5 and 6, and provides a long and uniform focal zone in elevation. The shape of auto-correlation of signals created by speckle is given by the shape of the beam. FIG. 7 shows the correlation of signals from two sequential frames at lag 0 as a function of the speed of scatterers moving in elevation direction. The values for the correlation are calculated assuming that the beam profile in elevation direction is Gaussian-shaped, with full width at half maximum (FWHM) of $\lambda \cdot f\_\#$, where $\lambda$ is the wavelength of the ultrasound pulse, and $f\_\#$ is the focusing strength. The transducer is assumed to have a center frequency of 10 MHz. The speed of sound is assumed to be 1540 m/s. The focus number, $f\_\#$, is set to 5.5. The PRF is 15 kHz, and the number of lines in the image is 192 giving a frame rate of 78 Hz.

Figure 8:
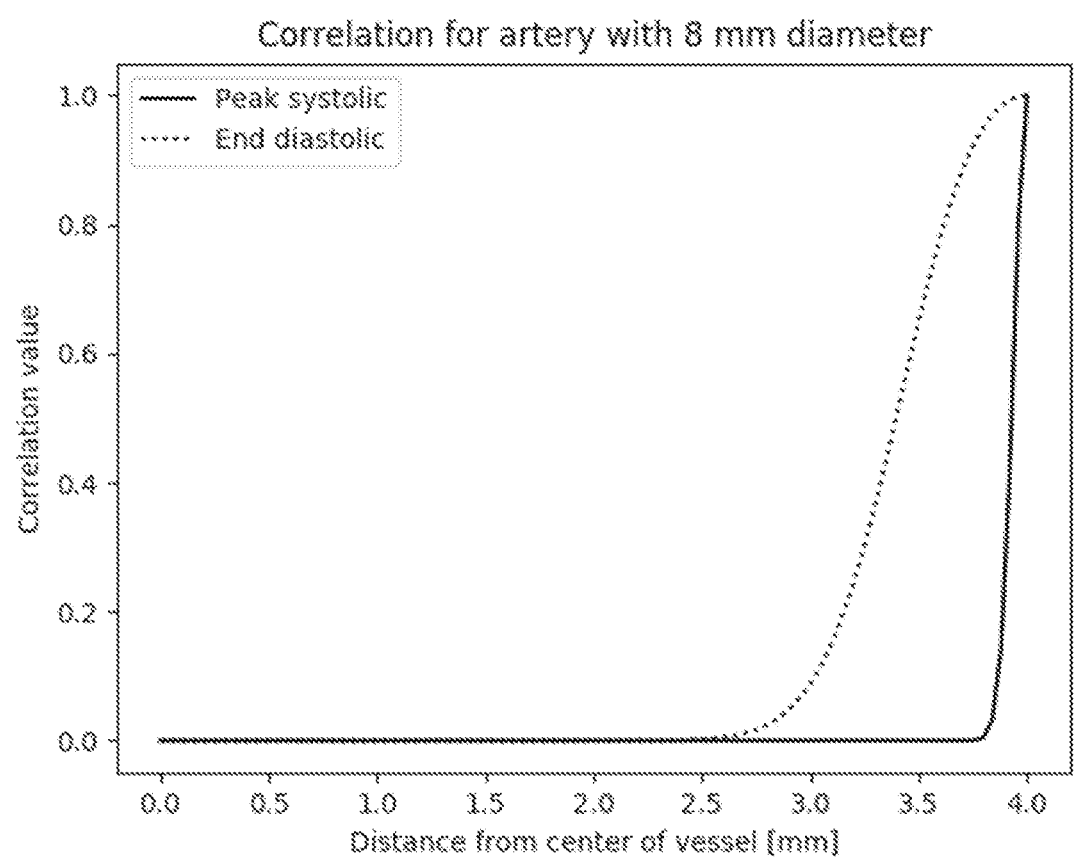
FIG. 8 illustrates a correlation value between the signals from sequential frames as a function of radial distance. The correlation is shown for peak systolic and end diastolic velocities. The frame rate is 78 Hz. The peak systolic velocity is 48 cm/sec and the peak end-diastolic velocity is 19 cm/sec. The flow profile is parabolic and is zero at the vessel wall. The flow is in a plane transverse to the imaging plane.

Based on the typical values for the velocities in the common carotid artery, and the profile of the beam in the elevation direction, it is possible to pre-compute expected correlation values for the flow in an artery. An example for the common carotid artery is illustrated FIG. 8. FIG. 8 shows the correlation value between the signals from sequential frames as a function of radial distance from the center of the vessel. The correlation is shown for peak systolic and end diastolic velocities. The frame rate is set to 78 Hz. The peak systolic velocity is 48 cm/sec, and the peak end-diastolic velocity is 19 cm/sec. The flow profile is parabolic and is zero at the vessel wall. The flow is in a plane transverse to the imaging plane. The vessel has a circular cross-section. The example uses the flow profile for an artery with diameter of 8 mm, shown in FIG. 5 and FIG. 6, and correlation values calculated for the transducer and imaging setup in FIG. 7.

The Detect CCA block 900 in FIG. 9 uses a classifier which receives two sets of features (1) estimates of the correlation at given pixel indicative of blood flow or noise, and (2) SNR Map which is indicative of regions with scattering from vessel walls, scattering from blood, and signals dominated by noise. The classifier implements a decision tree which has been trained using the supervised machine learning algorithm "Concatenated Decision Path," as described in I Mitzev, N. Younan 2017 "Concatenated Decision Paths Classification for Datasets with small Number of Class labels" ICPRAM, Porto Portugal, which is herein incorporated by reference. The training images are selected to be of size 1.5×1.5 cm, to ensure that the CCA is entirely inside the VOL. Then, a bounding box of size 1.5×1.5 cm is manually placed in each training image, such as the artery is in the middle of the box. A minimum of 200 images are needed for training of the classifier. Any window outside of the VOI is marked as Non-VOI.

Transducer Orientation Guide

Once the carotid has been identified or tagged, then the next step is to optimize the transducer orientation through rotation and translation until the cross-section of the carotid (transverse plane) is centralized in the acquired ultrasound image. This is accomplished through a user interface either on the display or on the transducer that guides the operator to rotate and translate the transducer. In one embodiment, the processor of the system implements the transducer orientation guide block 250 and calculates the ovality or non-circularity of the identified carotid in the B-mode images by segmenting the vessel wall and fitting the detected wall to an oval since a high ovality suggests the carotid is along the longitudinal axis. In another embodiment, the rotation of the oval major or minor axes relative to the normal to the skin line is also calculated to determine whether the image plane is near the longitudinal axis. The system identifies the position of the tagged carotid relative to the middle of the acquisition. Next, the system controls the user interface to guide the user through small incremental movements to obtain the ideal image. The ideal image plane is achieved when the tagged carotid is approximately in the middle of the acquired image with the minimum accepted ovality. When reached, the key data acquisition may begin.

Although the guide to minimizing the carotid ovality may be accomplished with a conventional transducer that only acquires one B-mode plane at a time, the expediency may be enhanced using a transducer that acquires multiple planes in real-time such as a 2D array, wobbler transducer, or transducer that can acquire perpendicular planes simultaneously. This allows the system to guide the user to ideal transducer placement through analysis of the volume data set by applying multiple cut planes through the volume. Each cut plane through the volume data set yields a different carotid ovality. Next, the user interface guides the user through transducer movements to the transducer orientation that yields this minimum ovality. If multiple planes are not available in real-time but spatial registration is, then a volume data set may be created over time by stitching multiple frames together which were acquired at slightly different acquisition times and positions to slowly guide the user to plane of minimum ovality.

Data Recording

The data recording block 210 is implanted by the processor using a cross-section of the carotid that enables the system to place the transmit foci at the ideal image depth to further improve contrast between the arterial wall and lumen. During the data recording, it is assumed that the operator knows enough about anatomy to move the transducer toward the bifurcation. Additional ultrasound image equalization and optimization may be done immediately prior to the full acquisition or during the acquisition as noted in the "Ultrasound Image Equalization and Optimization" section. As the transducer is moved, spatially registered frames are acquired and processed to help guide the operator to keep the carotid in the middle of the image acquisition. Multiple planes for compounding are also gathered to assist with arterial wall identification. This is again accomplished through small translations and rotations as the transducer is moved toward the bifurcation and the volume data set is acquired. Only after enough data is processed to guide the acquisition whereas RF element data is streamed to a memory device for future post processing and analysis using techniques found in Li, Pai-Chi and Li, Meng-Lin "Adaptive Imaging Using the Generalized Coherence Factor" IEEE Transactions on Ultrasonics, Ferroelectrics and Frequency Control, Vol. 50, No. 2 pp. 128-141 and Camacho, Jorge, Parilla, Montserrat and Fitch Carlos, "Phase Coherence Imaging," IEEE Transactions on Ultrasonics, Ferroelectrics, and Frequency Control. Vol 56, No 5, pp 958-974, which are herein incorporated by reference.

A priori knowledge of the carotid shape or direction is not assumed. Therefore, an insufficient length of the carotid may be initially obtained. The approximate ideal acquisition length is 5 cm which includes the bifurcation. Since the data acquired is a spatially registered volume, it is possible to calculate the length of the carotid included in the initial scan. If the length is deemed insufficient, then the system can recommend to the user to slowly move the transducer in the opposite direction to include an additional part of the carotid or a new scan can begin to include additional length.

Unlike the current diagnostic ultrasound systems which have multiple transducer ports or different transducers that can be connected to the ultrasound system, the disclosed device which is used for one application, assessment of artery health, has a permanently connected transducer to the system electronics. In one embodiment, the transducer includes an interface to help directionally guide the user during the semi-automated acquisition of the carotid data. It is preferable that this directional guide is in the same region of the acquisition (near the carotid) since it is hard to translate direction on a display to transducer movement especially for a nurse or a primary care physician.

Spatial Registration

The ultrasound acquisition may be accomplished with a conventional high frequency linear array; however, spatial registration is required to accurately represent the volume data set. This may be accomplished with different spatial tracking technologies:

Accelerometers, MEMs devices
2D arrays
Mechanical wobbler
Optical sensing
Magnetic tracking The ultrasound image plane coordinate system is registered to the tracking device coordinate system which enables spatial registration with the acquired ultrasound data. Only a couple technologies offer the possibility of gathering ultrasound volume data in real-time. The 2D array and mechanical wobbler help guide the user to optimally position the transducer prior to and during the acquisition. However, the 2D array and mechanical wobbler add cost and technical complexity to achieve spatial registration. Cost effective solutions to motion tracking include accelerometers and MEMs devices combined with the linear array which is the preferred embodiment.

In some cases, the current study being recorded may be compared against a previously acquired data set. In this case, the images and data from the current study can be immediately compared to images and data from a previous study during the acquisition. Since a data set already exists, the direction to move the transducer may be completely or partially determined by this comparison using correlation methods to determine the location of the transducer relative to previously acquired images and data. This information can be integrated with other methods such as ovality to determine the direction to tip and translate the transducer.

Temporal Registration

The artery wall diameter is affected by the pressure and therefore the cardiac cycle. Ideally, the images and data acquired can be temporally aligned to the entire cardiac cycle which includes systole and diastole since in most cases, it is best to perform most of the analysis during diastole. There are many methods to temporally register each acquired frame to the cardiac cycle:

1. Use multiple frames from the same vessel of interest and track the wall motion in three dimensions over the cardiac cycle. For example, diastole is determined when the distance between the proximal and distal walls is at a minimum.
2. Use of an external heart rate monitor (e.g. pulse oximeter, EKG, or other electrical methods)

The information from the heart rate monitor is attached to each acquired frame for later use by the analysis tool.

Transducer Orientation Guide During Recording

As mentioned, a characteristic to obtain confident results when applying this automated method of plaque detection is placement of the carotid in the center of the transverse ultrasound imaging plane throughout the volume acquisition (transducer orientation guide) with the transducer oriented as close to the transverse plane of the longitudinal axis of the vessel as possible.

There are many methods, other than just B-mode imaging, to keep the carotid artery in the middle of the acquired imaging plane and optimize the slice angle during the data recording:

Heart rate monitors which use optical reflection methods to determine heart rate can similarly be used to keep the carotid in the middle of the acquisition plane.
Forward Looking Image Guidance Acquisition (FLIGA) which uses information from the ultrasound image to give directional feedback to the operator
Photo-acoustics which uses the selective absorption of oxygenated and de-oxygentated blood with different optical wavelengths to identify arteries and veins Heart Rate Monitor One technique to locate the carotid and synchronize the acquisition to the heart rhythm is through optical reflection techniques, pulse oximetry. During the heartbeat, the amount of oxygenated blood increases and this can be detected using reflection techniques with near infrared or infrared light. This optical transmitter and receiver which operates at the appropriate optical wavelengths may be separate from the ultrasound device or integrated together. In one embodiment, two optical wavelengths are used to differentiate between oxygenated blood flow (arteries) and deoxygenated blood flow (veins) which is mounted with the ultrasound transducer to grossly locate the vessel.

Ultimately, the goal is to assist the operator in centralizing the ultrasound transducer on top of the carotid for the scan. If the devices are separate, then initially the optical device is scanned over the carotid to find the strongest signal. In one embodiment, the device records the location of the strongest signal and communicates the location to the ultrasound transducer coordinate system. The device is spatially registered using the tracking devices such as optical, magnetic, or a MEMs sensor. This global location determined with the optical device is then used to move the transducer to the same location using optical, magnetic, or a MEMs sensor. If the optical device is integrated with the ultrasound transducer, then registration is through mechanical relationships in the integrated device construction. A pulse monitor which is worn on the index finger or wrist may also be used to synchronize the ultrasound acquisition to the end of the heart cycle.

FLIGA

B-Mode

Figure 10A:
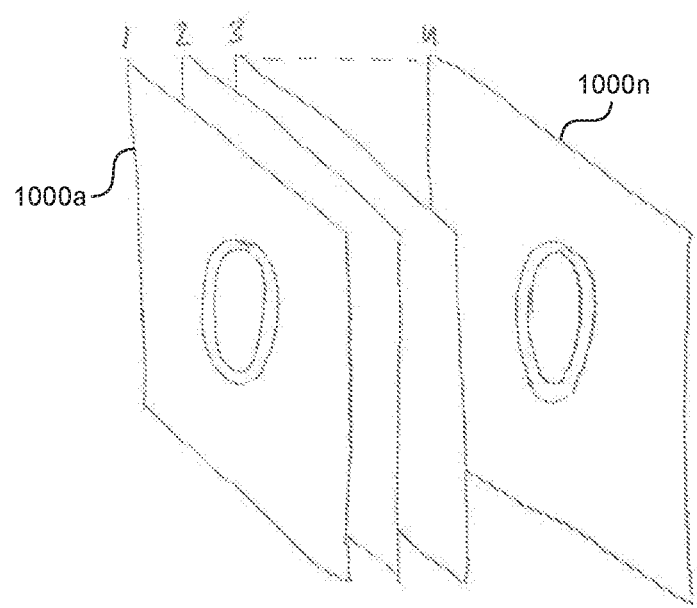
FIG. 10a shows multiple transverse ultrasound images.

FLIGA utilizes the technical advantages of ultrasound real-time volume acquisitions which are available through a mechanically rotated or translated linear arrays. It important to note that although this description describes the technique with a mechanically moved linear array, it is also possible with a 1.75D and 2D array. FIG. 10a shows the acquisition of multiple transverse planes 1000a-1000n with the carotid in the middle of the acquired data. The acquisition may consist of B-mode images, color Doppler (C-mode) images, power Doppler (P-mode) images, B-mode and C-mode, or B-mode and P-mode. Although regular B-mode is sufficient to track the carotid path, visualizing the blood flow in the carotid further confirms the direction. To guide the general practitioner which way to move the transducer during the acquisition, the transducer looks ahead to determine the carotid direction. Another significant benefit to FLIGA is the mechanical registration of the volume acquisition which enables accurate ultrasound plane stitching.

Figure 10B:
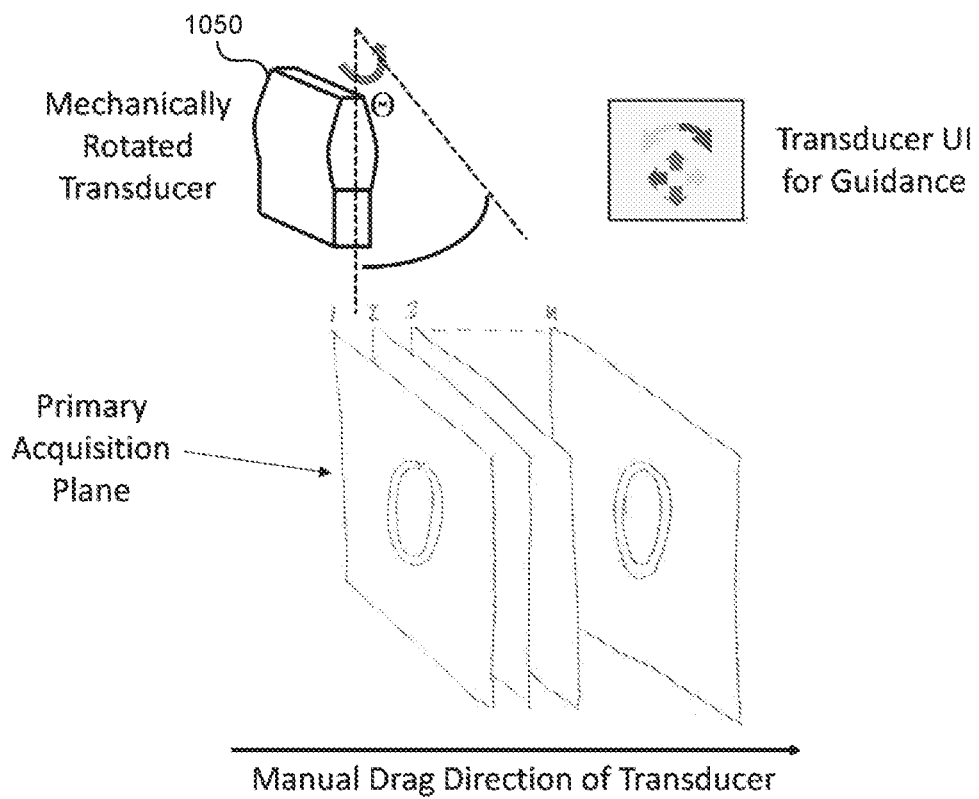
FIG. 10b shows a mechanically rotated transducer grabbing multiple planes with a corresponding user interface (UI) to give an operator guidance of which way to move the transducer during a scan in accordance with some embodiments of the disclosed technology.

FIG. 10b has added the linear array transducer 1050, which in this case, is rotated in the direction of future manual motion. It is important to note that the transducer 1050 may also be translated or translated and rotated or rotated in this direction. It will be shown later that transducer rotation may offer benefits over just translation due to depth changes in the carotid along the acquisition path. The amount of transducer rotation relates to the manual speed of the transducer when dragged across the skin surface which is similar to the amount of 'look ahead' required when driving at fast speeds on the road where the amount of time to adjust direction is considered because of the distance traveled prior to making the decision. Ideally, the manual speed of the transducer would be slow enough to limit the rotation angle and allow for acceptable frame rates, line densities in each frame, and sufficient information over the cardiac cycle. The spacing between acquisition planes may be adjusted since the carotid does not change direction quickly although a finer sampling assists with motion tracking and eventual stitching and compounding of the multiple acquired planes and volumes. The VOI around the carotid can also be limited to reduce the overall number of vectors required for image acquisition.

Figure 11A:
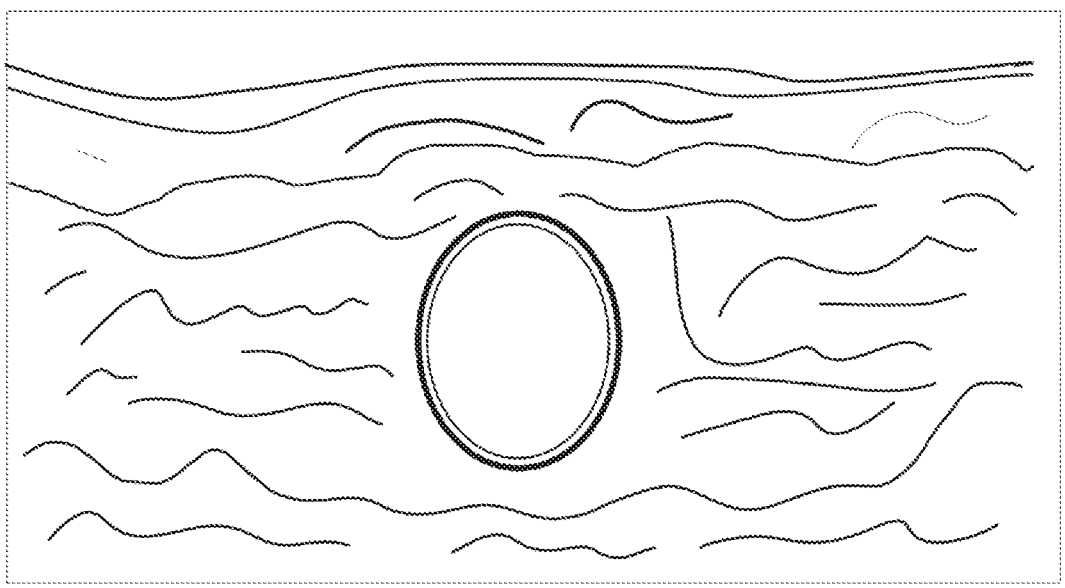
FIGS. 11a and 11b illustrate the position of an artery in two ultrasound images with manual motion.
Figure 11B:
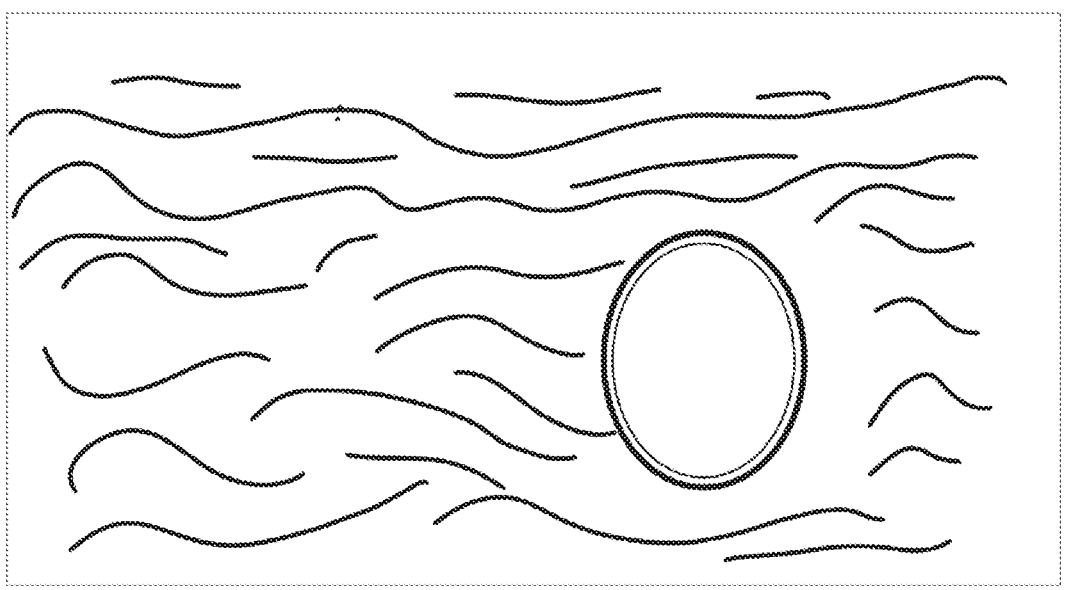
Figure 11C:
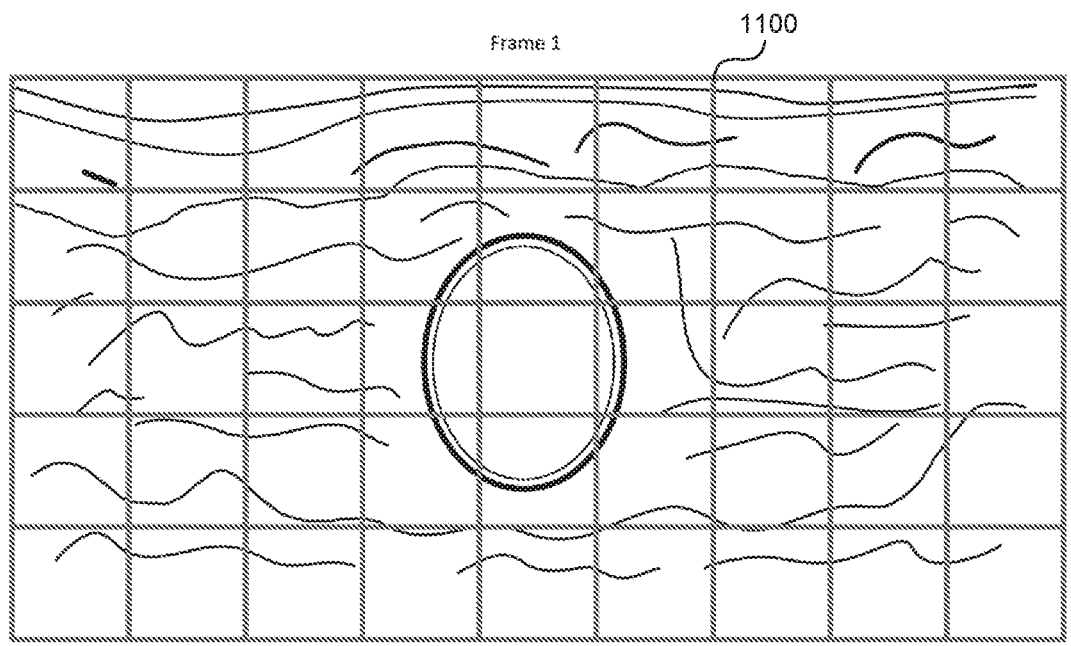
FIGS. 11c and 11d illustrate ultrasound images subdivided with one region highlighted for motion estimation.
Figure 11D:
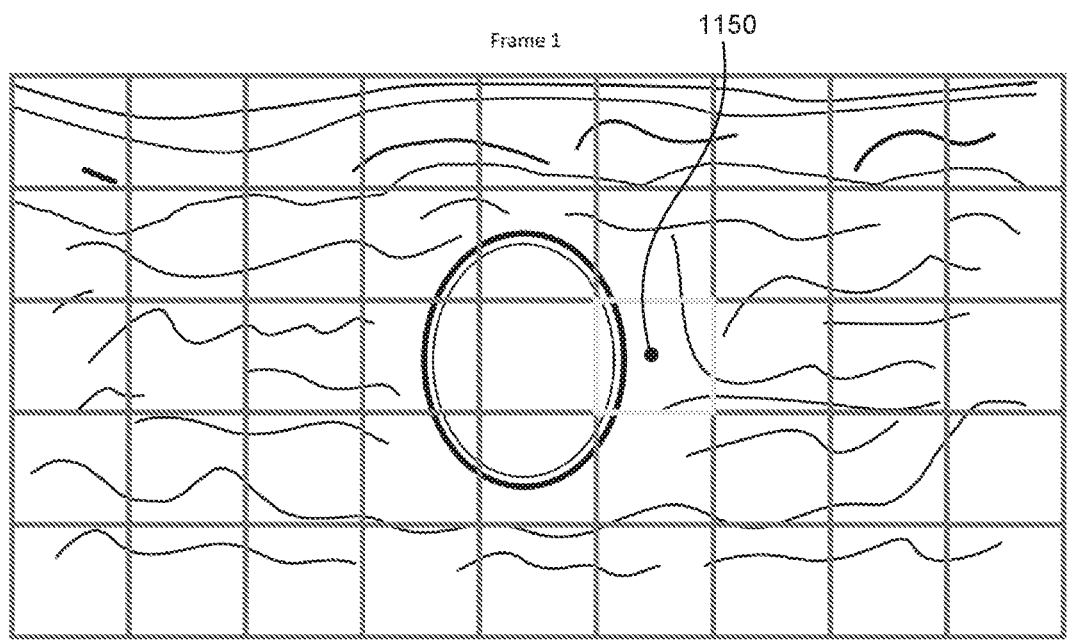
Figure 11E:
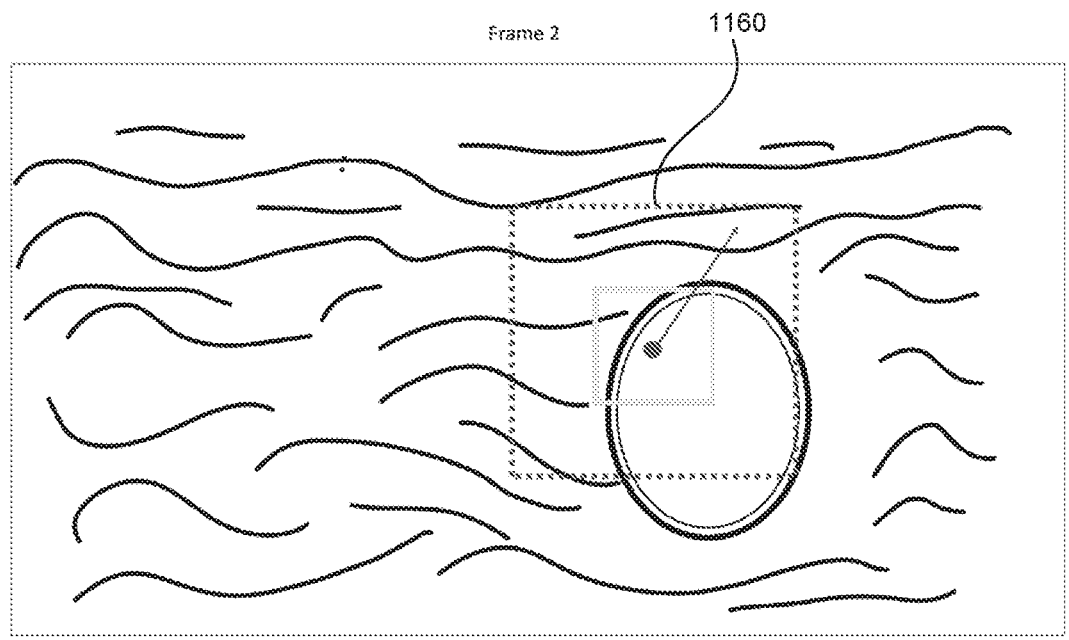
FIG. 11e shows a box moved over a region in an ultrasound image to find a direction of movement of a carotid in accordance with some embodiments of the disclosed technology.

Since the multiple planes are mechanically registered out-of-plane, only the azimuth (x-axis) and depth (z-axis) directions of the carotid need to be determined. In general, the system assesses the direction of the carotid from the current imaging plane to future imaging plane in order to direct the operator which way to move the transducer. FIGS. 4a and b show two ultrasound images gathered with the transducer. Frame 1 (FIG. 11a) is the ultrasound image which is directly below the transducer and considered the current acquisition plane whereas Frame 2 (FIG. 11b) is the ultrasound image for a future image acquisition which is in front of the transducer and in the direction of manual motion. FIG. 11c shows Frame 1 subdivided into multiple regions 1100 for purposes of determining the motion direction between Frames 1 and 2. The size of subdivided regions 1100 can be varied depending on the transducer characteristics, the overall line density and number of pixels, and size of features of interest. Each subdivided region 1100 from Frame 1 is compared to the same region in Frame 2. FIG. 11d highlights one subdivided region 1150 in Frame 1 which will be directly compared to Frame 2 for a variety of possible positions. The subdivided region is moved over a possible search region 1160 in Frame 2 (FIG. 11e) noted by the red box to determine the general direction of the features between the frames. This possible direction is determined using a 2D cross-correlation calculation:

$$\gamma(u, v) = \frac{\sum_{x,z}[F2(x, z) - \text{mean}(F2_{u,v})] * [F1(x-u, z-v) - \text{mean}(F1)]}{\left\{\sum_{x,y}[F2(x, z) - \text{mean}(F2_{u,v})]^2 * \sum_{x,y}[F1(x-u, z-v) - \text{mean}(F1)]^2\right\}^{0.5}}$$

where F2 is Frame 2 and F1 is Frame 1 and $F2_{u,v}$ is the region in Frame 2 that includes the location of the Frame 1 subdivided region which has been shifted by u and v. The location of the maximum correlation given a minimum value is considered the direction of the subdivided region between Frame 1 and Frame 2.

The mean motion between Frames 1 and 2 is determined by averaging the u and v distances for maximum correlation for each subdivided region.

$$u(F2, F1)_{mean} = \frac{\sum_{R=1}^{S} u(F2, F1)_R}{S}$$

$$v(F2, F1)_{mean} = \frac{\sum_{R=1}^{S} v(F2, F1)_R}{S}$$

where $u(F2,F1)_{mean}$ and $v(F2,F1)_{mean}$ are the estimated directions in azimuth and elevation between features in Frame 1 to similar features in Frame 2.

In one embodiment, the system gives directional guidance to the operator to keep the carotid in the middle of the B-mode image by estimating the displacement between the frames of an object or region using correlation methods which is mathematically combined with the amount of out-of-plane rotation and/or translation.

Figure 12:
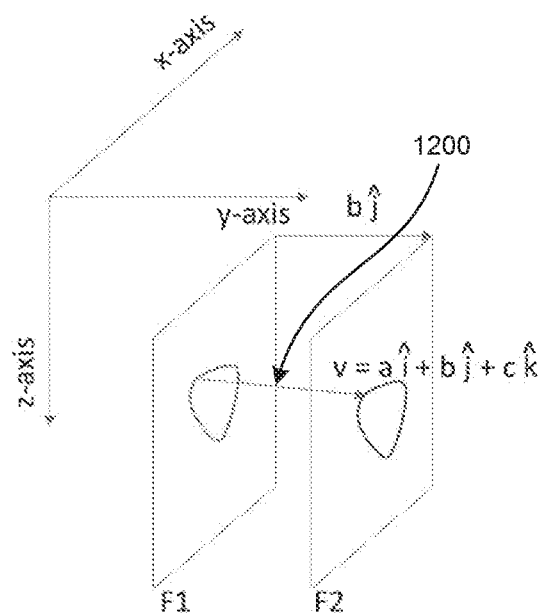
FIG. 12 illustrates a translation vector between image frames.

FIG. 12 shows the translation vector 1200 between the two frames, F1 and F2. The distance between the two frames is 'b' and is determined by the mechanical rotation and/or translation of the transducer. The distances 'a' and 'c' are determined through the 2D cross correlation calculation previously discussed. In one embodiment, a processor of the system is programmed to calculate incremental displacements by looking at the difference between multiple registered frames to determine the recommended transducer path over the region imaged which moves the center of the carotid back to the middle of the imaging plane.

These calculations only determine the transducer translation and not the rotation about the z-axis. In some cases, it may be advantageous to orientate the transducer such that the imaging plane cuts the short axis of the carotid. To place the imaging plane over the short axis, a sufficient number of frames is acquired to assess the tissue volume and estimate the location of the carotid short axis relative to the transducer. The amount of transducer rotation is determined by applying multiple cut planes at different angles through the volume. The cut plane that yields the smallest area of the carotid is compared to the transducer orientation to determine the required angular movement by the operator. Once the optimal angle is obtained, the vessel of interest (VOI) with the carotid can be compared to the entire acquired volume to recommend the rotation of the transducer as it is manually dragged across the transducer.

B-Mode with Doppler

There are other methods to assist the operator with the transducer rotation and direction of translation. Color Doppler, power Doppler, or other ultrasound blood flow techniques may be deployed to estimate the direction of the flow when acquired 3D. The 3D measurement of blood flow yields both the transducer translation and rotation directions.

Figure 13A:
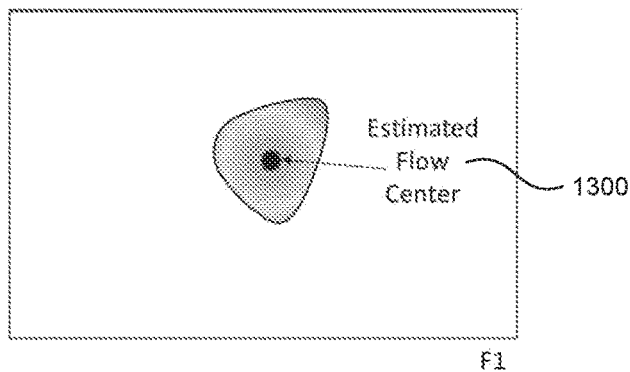
FIG. 13a shows a center of flow determined in a frame using a center-of-mass approach to the detected flow.
Figure 13B:
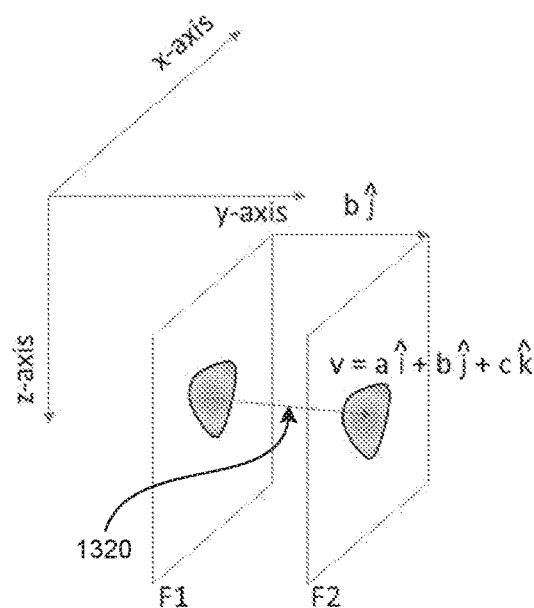
FIG. 13b shows a center of flow approach applied to two frames such that the translation vector is determined.
Figure 13C:
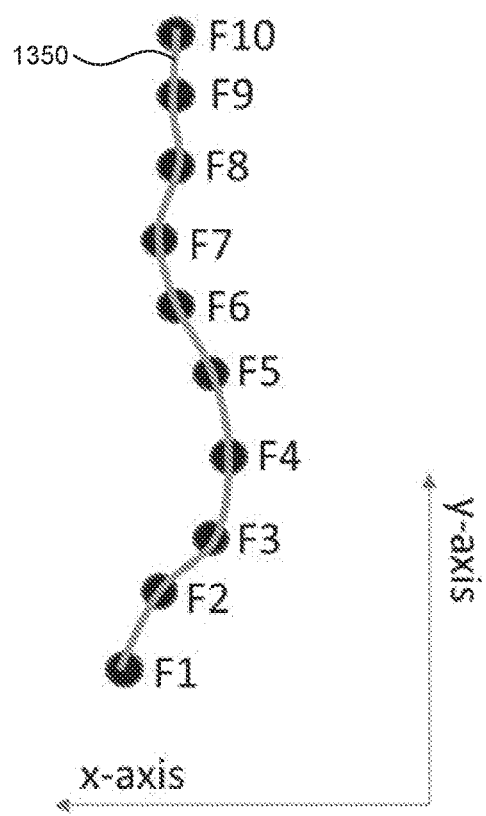
FIG. 13c shows a map of the carotid in the x-y plane by putting together multiple translation vectors.

Since the flow is volumetric, a weighted center of mass technique on each frame may be applied to determine the 3D carotid path as shown in FIGS. 13a, b and c. In one frame, the flow center 1300 is estimated around the carotid (FIG. 13a). This same method is applied to the next frame such that a translation vector 1320 between the two frames can be estimated (FIG. 13b). If this is applied to all frames in the acquisition, the blood flow path 1350 in the carotid may be estimated in the x-y plane (FIG. 13c). In this embodiment, the flow in the vessel aligns with the orientation of the carotid walls and the system calculates how the operator should rotate the transducer such that the imaging plane is approximately orthogonal to the flow direction. This is accomplished by determining the normal to the directional vector of the flow and recommending the path to follow when acquiring the spatially registered volume scan. Using flow methods has advantages over B-mode techniques such as:

- Multiple cut planes are not necessary to initially determine optimal transducer rotation
- Calculation intensive 2D or 3D cross correlations are not required
- Center of flow can be weighted based on the flow velocity These methods may be combined with the previous techniques described to further enhance the carotid direction detection and feedback to the operator.

Photo-Acoustics

Another method for determining the track of the carotid artery is the use of photo-acoustics which requires an optical transmit aperture integrated with an ultrasound imaging transducer used in receive only. This type of imaging distinguishes veins and arteries due to the optical absorption of oxygenated blood versus deoxygenated blood see Neuschler, Eric I, Stavros, A. Thomas, Lavin, Philip T and Ulissey, M. J. "Diagnosis of Breast Masses Using Opto-Acoustics," American Roentgen Ray Society M.S. PowerPoint Presentation pp. 1-40. For example, Seno Medical has used this technique to improve the diagnostic confidence of breast lesions. In the Imagio System, independent pulses of light at 757 nm and 1064 nm are illuminated on tissue to create a thermal-elastic effect. The immediate absorption of light by tissue creates an acoustic wave that can be detected by an ultrasound array of receivers as described in Oraevsky AA Optoacoustic Tomography of the Breast, Chapter 33 "Photoacoustic Imaging and Spectroscopy" L. Wang, Taylor and Francis Group, New York 2009. Veins are distinguished from arteries using light since the shorter wavelength is more readily absorbed by deoxygenated blood whereas the longer wavelength is more readily absorbed by oxygenated blood. Like the Doppler method previously described and captured in FIGS. 13a-13c, in this embodiment, the system maps out the depth and lateral position of the carotid to assist the manual acquisition of the ultrasound volume data set by applying the photo-acoustic effect which differentiates regions of blood flow with other tissue types. The processor stitches the data from the photoacoustic device to the ultrasound image data to guides the direction the operator should move the transducer. In this case, the acquisition of photo-acoustic images would be interspersed between transmit-receive ultrasound data acquisitions. The acquisition of two different sets of images using different technologies has distinct advantages:

- Registration of the carotid artery is achieved with pulse-echo methods and photo-acoustic methods, this offers another method of image compounding beyond ultrasound compounding to enhance the edge of the lumen-intima boundary
- Having the photo-acoustic method along with pulse-echo data adds a unique way to apply coherence factors which improve the image contrast and resolution around the carotid. This includes the generalized coherence factor [2], phase coherence factor and sign coherence factor [3]. In one embodiment, the system calculates coherence factors from two data sets to improve contrast of the vessel wall to the lumen by analyzing the echo data from the photo-acoustic system and the pulse-echo ultrasound data prior to image generation.
- In another embodiment, the system improves the resolution of the ultrasound image through comparison of mages between the two methods, photo-acoustics and pulse-echo imaging since photo-acoustics minimizes the amount of aberration which occurs between transmit and receive.

Carotid flow detection using photo-acoustics does not have directionality challenges like ultrasound Doppler.

Other Tracking Methods

The previous paragraphs highlighted the primary methods of tracking the carotid; however, there are other methods that only require a 1D linear array with a motion tracking system. In one embodiment, the system spatially registered the frames in three dimensions by using an optical, magnetic, MEM sensor to create the registered 3D volume. One method to obtain registration of the frames is through the use of magnetic tracking. In one embodiment, the frames are spatially registered through a magnetic transmitter which acts as the origin of the coordinate system and a magnet receiver which is placed in the ultrasound transducer which is at a known location from actual linear array. This setup enables three-dimensional registration of the ultrasound images. A software algorithm is used to determine the transverse plane to the artery. If the patient tends to move considerably, a second receiver may be located next to the acquisition area to try to account for this motion. However, since in most cases adults are scanned with this system, it is highly likely that they would be able to remain still for the duration of the acquisition.

In addition to adding the magnetic tracking system to assist with frame spatial registration, in another embodiment, the system tracks the spatial location of the transducer using three-dimensional acceleration sensors to detect motion and determine incremental movement which assists with overall tracking. This is similar to the technology used in gaming systems such as the Nintendo WII Best, Shivali, "The Future of Medical Scans?" Nintendo Wii-inspired 7 Pound Microchip turns D2 Ultrasound into 3D Imaging devices" DailyMail.com, Oct. 31, 2017.

In another embodiment, optical tracking is another method that is used to register imaging frames. In this case, distances from an optical transmitter to the object are measured using a reflection method which is similar to methods used in gaming systems such as the Xbox Kinect. Rather than using a global optical tracking system, a local optical tracking system which either uses the surface of the skin or an applied skin marker may also be used for registration.

In another embodiment, the system registers the device location using an ultrasound three-dimensional tracking system which does not require a 2D array or mechanically moving transducer, but some satellite transducers as described in U.S. Pat. No. 8,167,805 B2 or two orthogonal planes as captured in U.S. Pat. No. 6,537,220 B1.

It is important to note that some of the spatial registration methods do not obtain volume data or look ahead at the artery position as in the case of FLIGA to recommend the correct transducer movement prior to scanning a specific region. The algorithm suggests only which way to move the transducer to keep the artery in the middle of the 2D image. Furthermore, identification of the transverse plane occurs in software once a sufficient number of images are acquired to determine the cut plane that creates the minimal flow area.

Motion Artifacts

It is expected that motion artifacts will negatively affect the acquired images. These motion artifacts may be caused by:
1. Pulsatile flow which causes expansion and contraction of the artery walls
2. Breathing
3. Swallowing or talking
4. Neck motion It is expected that a slow acquisition, image analysis through software, ultrasound image analysis and patient instruction minimizes most of these motion artifacts by selecting the best frame-to-frame match. Other methods include using pulse oximeters, EKG signals or breathing sensors identify which frames occurred at the same point of the cardiac cycle.

Bifurcation

Plaques have a higher probability of forming where the common carotid splits into the internal and external carotids also known as the bifurcation. This is primarily due to the turbulent flow near this juncture. A better assessment occurs when the bifurcation is included in the overall scan to assess the patient risk. As will be discussed in the Use Case Description, the bifurcation may also be used to signify where the scan should stop. Although this split occurs, the previous techniques are still applicable because a weighted average of measured flow of the image still gives a general sense of the carotid direction. Frame-to-frame comparison also enables the split of the bifurcation to be tracked using just B-mode images.

As the transducer moves, the position of the carotid is tracked. The transverse shape of the contour changes from oval, common carotid, to a union of two circles (with dip in the middle), an indication of the bifurcation to two separate ovals corresponding to the internal and external carotid arteries. Although the two separate ovals are distinguishable from the common carotid, sufficient spatial sampling between planes along with the identification of the union of two circles enables tracking through the transition.

Figure 14:
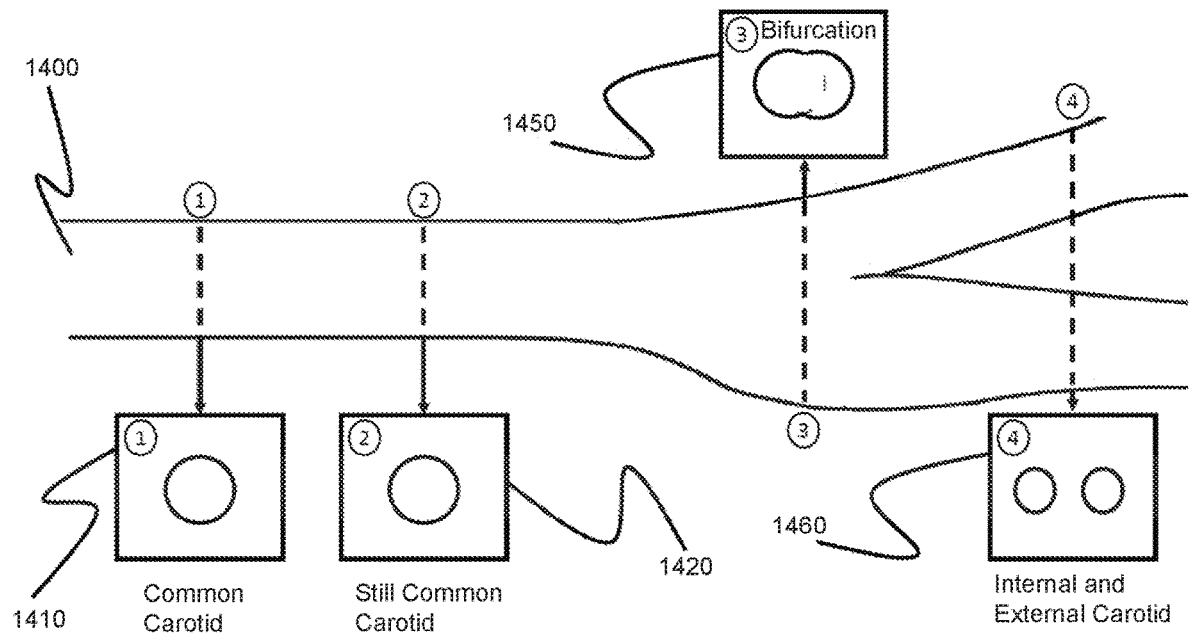
FIG. 14 illustrates visual cues to a region of the carotid that is being scanned. The device is programmed to use different protocols for different vessels.

The changes in the shape of the contour, as the scan progresses are illustrated in FIG. 14 showing a number of transverse slices 1410, 1420 of the CCA 1400 up to the point of bifurcation 1450 where the image looks like two joined vessels. Past the point of bifurcation, the carotid splits into two separate vessels 1460.

Figure 15:
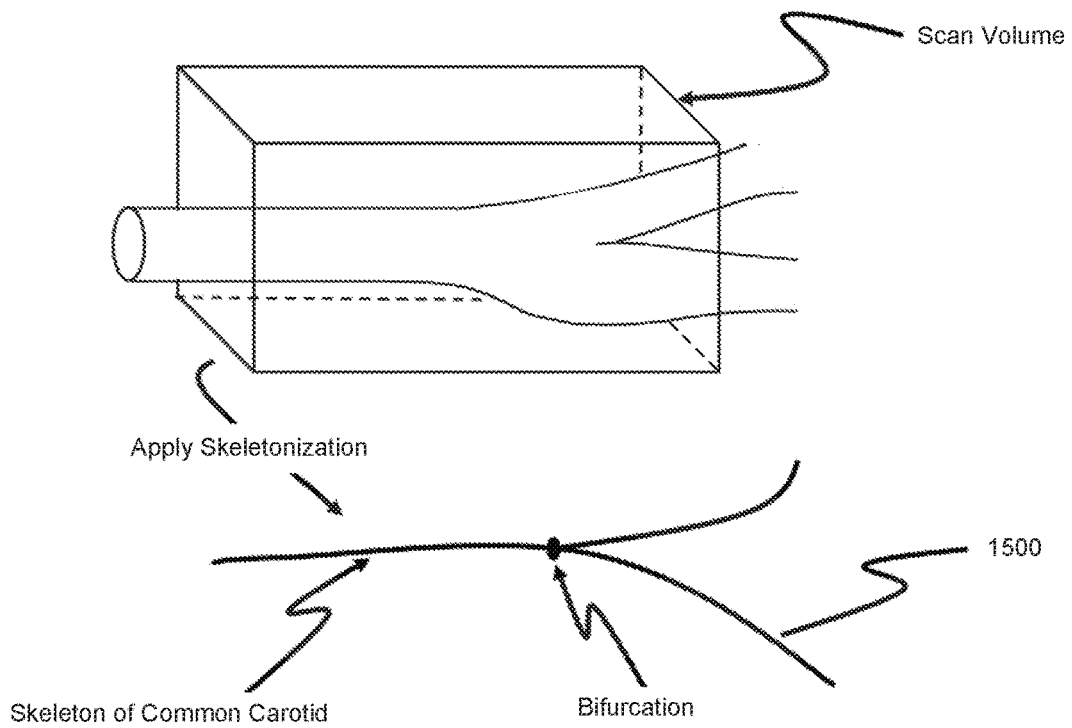
FIG. 15 shows the detection of a scanned region using skeletonization.

After the volume is acquired, the carotid artery is segmented and a skeletonization algorithm is applied as shown in FIG. 15. The knot (junction) 1500 where the inner, outer and common carotid arteries meet is a feature that is used to determine whether a sufficient portion of the artery has been scanned.

The length of the scan before and after the bifurcation is set to 4 and 1 cm respectively. This ensures repeatability of results. The skeleton of the artery is also used to align old and new measurements for follow-up investigations.

Other Peripheral Arteries

In other embodiments, similar techniques are applied to other major peripheral arteries such as the brachial, radial, ulnar, iliac, femoral, popliteal, tibial, and peroneal. In each case, anatomical landmarks are used to identify where the exam begins and ends. For example, the inguinal crease may be used to identify the start of the femoral artery.

Veins

As mentioned, the previous techniques apply to arteries and veins. Veins are differentiated from arteries by:
1. Slower flow
2. No pulsatility
3. Location near the skin surface
4. Veins collapse with light pressure To apply this algorithm to veins, in one embodiment, pulsatility at the vessel wall or flow rates in the vessel are automatically detected to guide the user on how quickly the transducer and to identify the vessel type. An external pressure sensor or small standoff integrated into the transducer prevents the user from accidentally applying too much pressure which collapses the vein.

High Level System Diagram

Figure 16:
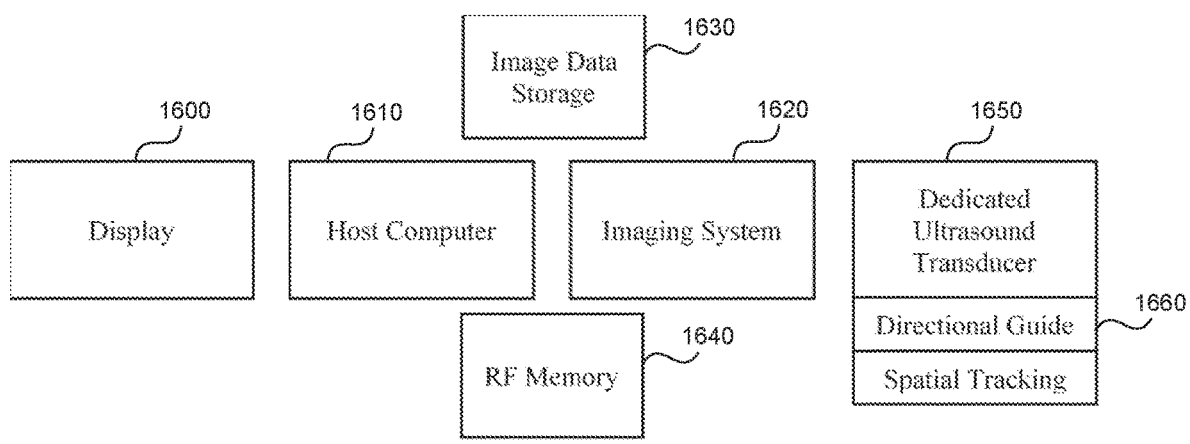
FIG. 16 shows a high-level block diagram of a system for detecting atheroma in accordance with some embodiments of the disclosed technology.

As shown in FIG. 16, The electronics of the system consist of a display 1600, a host computer 1610 (e.g. processor, CPU, GPU or the like) for managing the user interface, an ultrasound imaging system with transmit and receive electronics 1620, and memory 1640 for post-processing of RF data and image data 1630 to guide acquisition. In one embodiment, the display, host computer, imaging system, image data storage or rf memory is within the handheld device. FIG. 16 shows the device high-level block diagram where the ultrasound transducer 1650, spatial tracking and directional guide are integrated in the same system. When the system calculates the way to move the transducer, then this is communicated from the host computer 1610 to the directional guide 1660 of the transducer light up to help the user move the transducer in the optimal direction.

As mentioned above, in one embodiment, the system is sequenced through the states/blocks mentioned in FIG. 2 which leads to the volume and RF acquisition for analysis. The imaging system contains the transmit and receive electronics necessary to electronically focus and steer ultrasound beams. Because of the real-time nature of the acquisition, the ultrasound image planes are predetermined. This includes multiple image planes at different steering angles, typically three or more, which assist with identification of the entire carotid perimeter which improves the ovality calculation. The spatially registered image planes processed during the acquisition are stored as image data and may be referenced to guide and complete the acquisition. The element RF data from these acquisitions is saved in a separate memory location for analysis after the acquisition is completed. The saving of RF data permits the application of unique methods which enhance the contrast between the wall and lumen further improving the diagnostic measurement. Metadata such as attached to the processed image and RF data to help with post-processing and spatial registration. The host computer (processor) and processor executes programmed instructions stored in a computer readable media (memory, hard drive etc.) to perform multiple tasks which includes one or more of the following:

Performing system initialization and checks
Registering the patient (e.g. with the ultrasound system processor and display)
Determining the user interface states on the display
Acknowledging user inputs and displaying appropriate outputs
Performing the real-time and post analysis on the image and RF data
Comparing previous studies with the current study of the same patient to monitor carotid health improvement Data Quality Confirmation After the acquisition is complete, the data is assessed to determine the overall quality. There are many characteristics that determine the quality of the data (block 220 FIG. 2). These characteristics include one or more of:
- Wall continuity
- Contrast between wall and lumen
- Acquisition length
- Artery ovality in ultrasound imaging plane
- Angle between imaging plane normal and artery longitudinal axis Some or all of these parameters may be combined into one factor to reflect the acquisition quality. In some cases, quality thresholds will be established to determine whether the acquisition should be repeated.

Use Case Description in the Case of Carotid Imaging

Figure 17A:
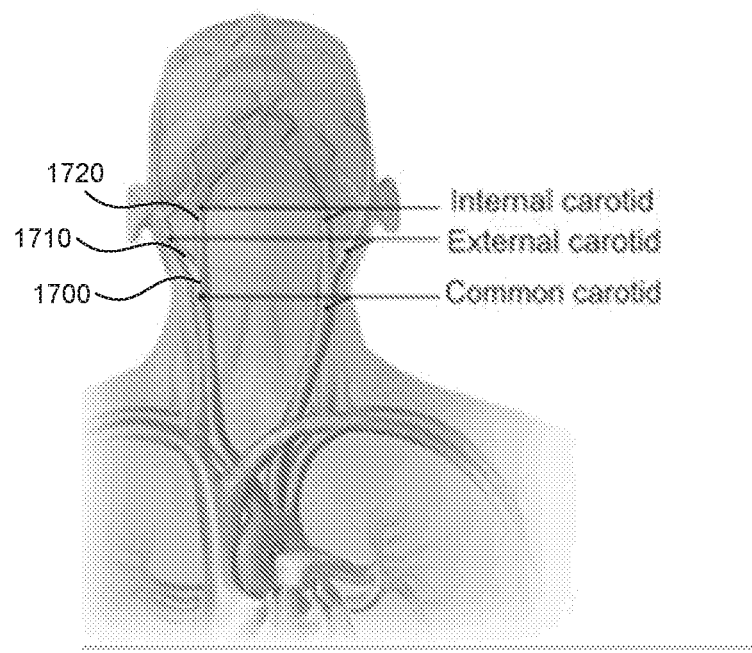
FIGS. 17a and 17b show the location of the common carotid and a placement of an ultrasound transducer for a scan.
Figure 17B:
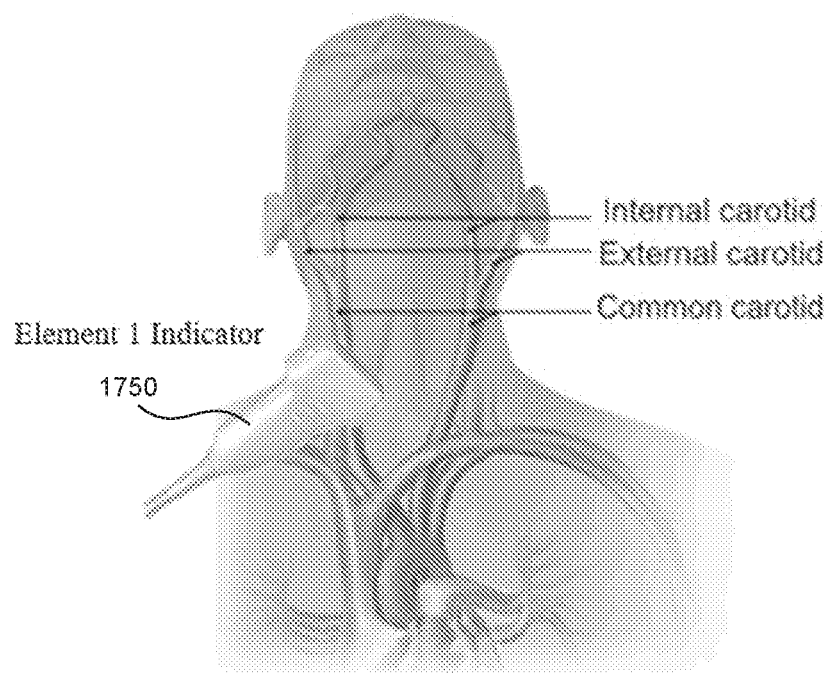

The exam begins by placing the transducer near either the right or left carotid where the ultrasound images will be acquired. FIG. 17a shows a front view of the common carotid 1700 as well as the external 1710 and internal carotid 1720. The common carotid enters the neck area slightly to the left (~25 mm to 50 mm) of the clavicular notch which is where the exam begins. This is because the clavicle and clavicular notch are easy reference points to find on most patients. The linear array 1750 is placed just slightly above the left clavicle with the element number one indicator to the left as shown in FIG. 17b. The initial placement of the transducer can be estimated by manual palpation which gives an acceptable assessment of the common carotid location and general placement of the ultrasound transducer.

Upon placement of the transducer on the neck, the system continuously checks for ultrasound backscatter and when recognized, asks the operator whether the image backscatter should be optimized and equalized in the current location. This is completed through an actuator on the transducer, a virtual control on the display, or an actuator on the system.

Figure 18A:
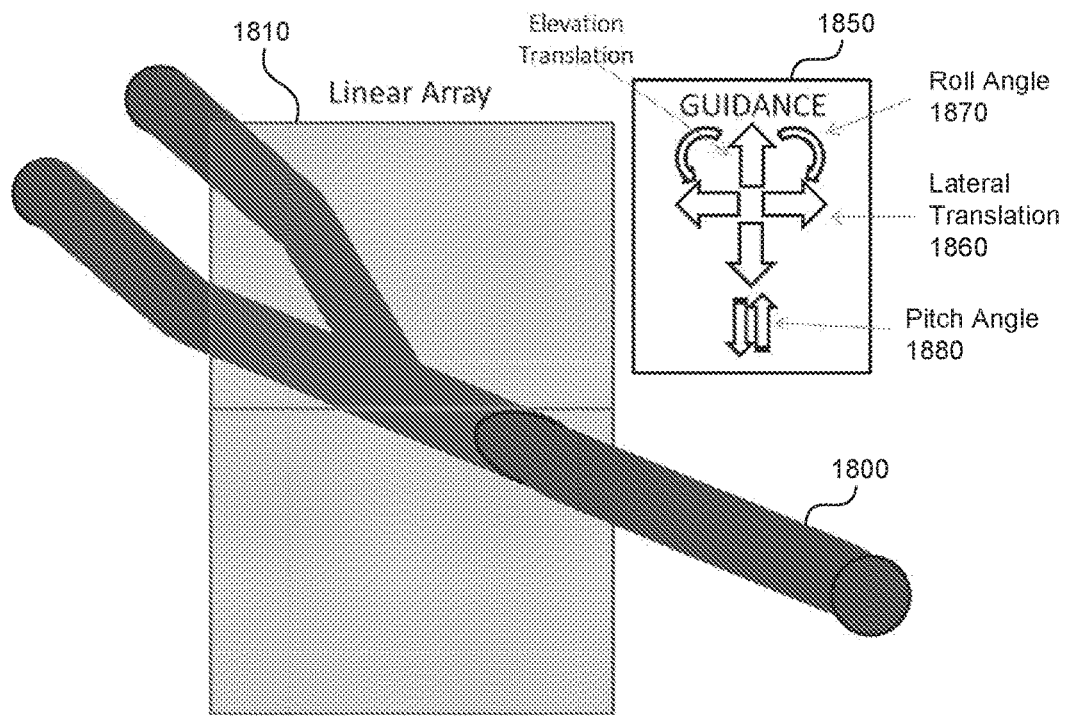
FIGS. 18a-18c show a carotid in an imaging plane along with guidance on a transducer user interface to move the carotid into a center of the image in accordance with some embodiments of the disclosed technology.

The next step in the acquisition is the carotid tagging and transducer positioning to start the acquisition. FIG. 18a shows a 3D sketch of the carotid 1800, the transducer placement 1810, and the transducer guidance system 1850 on the transducer. The transducer guidance consists of arrows 1860 to recommend transducer translation left and right (lateral) or forward and backward (elevation). Two types of rotation are also identified in the image guidance, roll indicators 1870 and pitch indicators 1880. Roll is the rotation angle which is about the normal to the linear array surface. The pitch is the angle about the axis that rotates through the row of linear array elements. It is important to note that the yaw of the transducer could be added to the transducer guidance, however, it was not mentioned because it is not considered a necessity. The amount the user should change the yaw angle is dependent on the gel layer describe by the system.

Figure 18B:
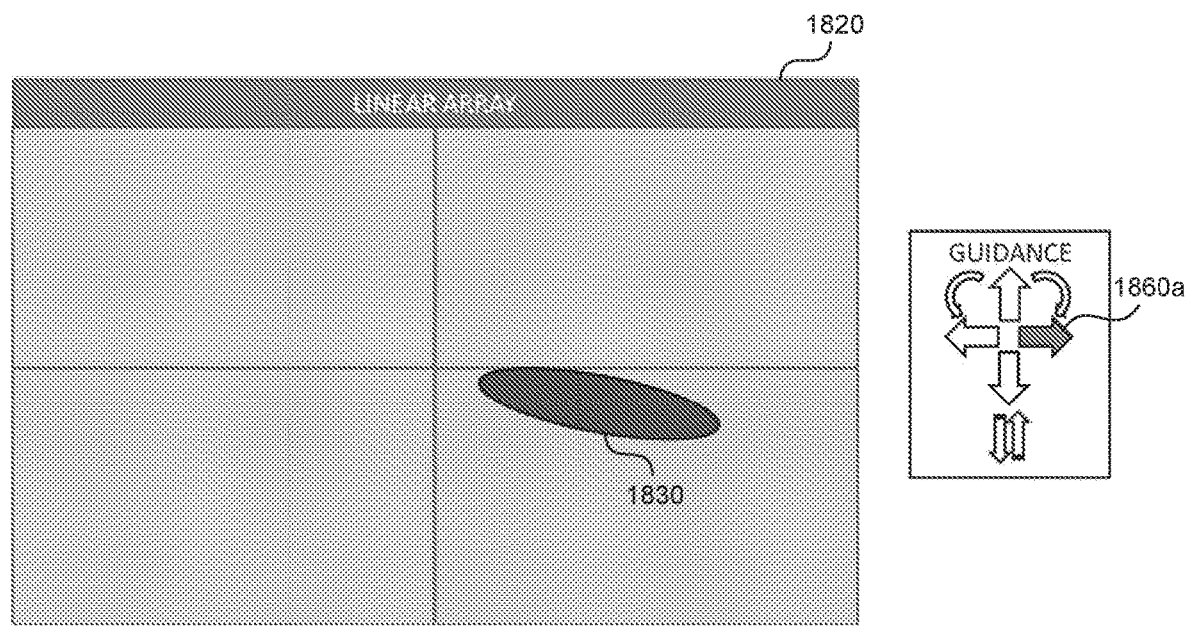

It is not anticipated that the carotid will even be present in the initial imaging acquisition. In this case, the system notices the absence of the carotid and asks the operator to continue searching. The operator in turn moves the transducer toward the position where the carotid was felt through manual palpation. Once the imaging plane includes a sufficient cross-section of the carotid and this is detected by the ultrasound system, the system either gives an audible beep, a visual or tactile response to the operator. This signals that the carotid has been located and the optimization to the transverse plane can start (FIG. 18a). The carotid tagging may be done automatically through machine learning methods or manually by selecting the lumen on the image. FIG. 18b shows the resulting imaging plane 1820 based on the intersection with the carotid 1800. In this case, the cross-section of the carotid 1830 is elongated laterally and off center. The goal is to move the transducer about the carotid such that the cross-section is approximately centered to the linear array and improve the angle of the imaging plane, so it is closer to the ideal transverse plane as determined by the carotid longitudinal axis.

As just mentioned, it is not expected that the carotid cross-section will be in the middle of the B-mode image. Furthermore, the acquired cross-section may not be at an acceptable angle which will require the operator to get closer to the ideal transverse plane. The system guides the operator to center the carotid in the middle of the B-mode image. For example, if the carotid is toward the right of the image as in FIG. 18b, then the guidance system recommends the operator moves the transducer to the right. Notice how a right arrow 1860a in the transducer guidance is green. Colors of the arrows, brightness, audible cues or percentage the arrow is lit may help determine whether the carotid cross-section is within an acceptable region laterally and guide the operator which way the device should be moved. The position of the carotid relative to the linear array affects the achievable VOI resolution and analysis accuracy. It is not necessary for the operator to place the carotid exactly in the center of the acquired image. It just needs to be sufficiently in the middle such that the maximum number of elements are used to optimize the VOI resolution and contrast. The acceptable range of this position depends on the array length, number of elements, element pitch, and operation frequency.

Figure 18C:
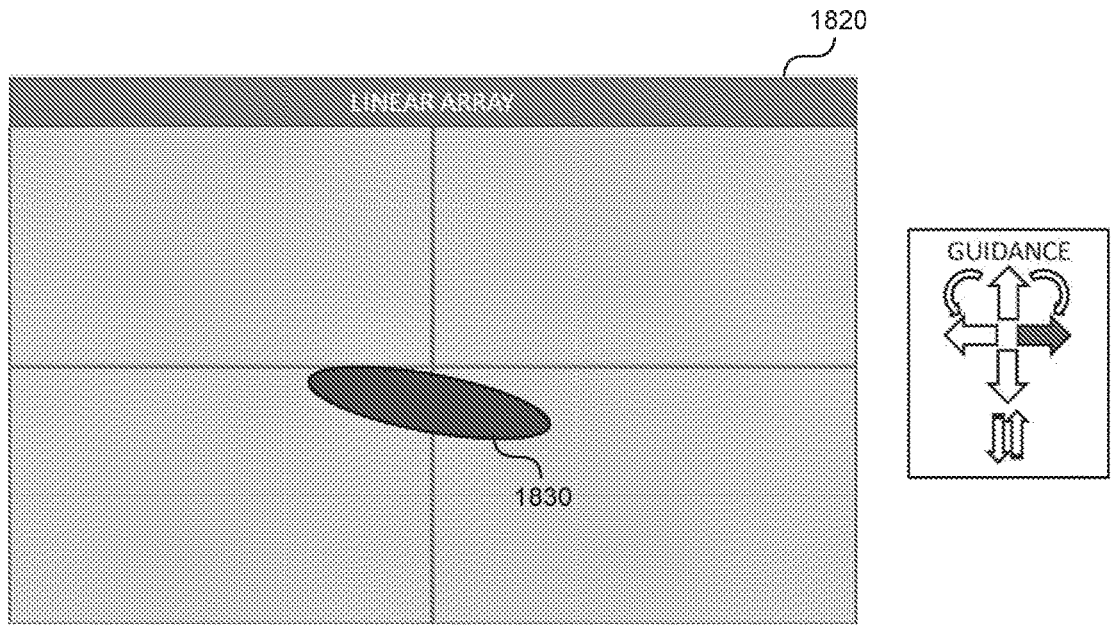

FIG. 18c shows the carotid cross-section 1830 successfully moved to the middle of the B-mode image 1820. The image guidance may change the arrow color, give an audible or tactile cue to signify the carotid is sufficiently centered. It is important to note that once the carotid is tagged, then it is much easier to track the position. This is because the lumen and arterial wall as well as potentially other features may be used to identify the VOI and object from frame-to-frame.

Once the carotid is sufficiently centered in the image, in one embodiment, the system assesses characteristics of the carotid to determine if the acquired plane is close enough to the ideal acquisition plane by comparing the ideal image plane angle to the actual acquisition. The ideal acquisition plane has the carotid in the middle of the image and is normal to the carotid longitudinal axis. The characteristics assessed include one or more of:
1. Length of the carotid axis in depth
2. Width of the carotid axis in azimuth
3. Ovality or noncircularity which is a measure of the difference between the major and minor axis of the carotid. In most cases, the ovality will be close to 0. A range of acceptance is acquired.
4. The rotational orientation of the major and minor axis. This angle should be close to normal to the linear array.
5. The contrast of the identified arterial wall to the lumen which is typically maximized at the right incidence angle Since the length and width of the carotid are limited anatomically, ranges can be used to determine acceptance of the roll and pitch angles. The carotid cross-section is fit to an ellipse to identify the major and minor axes, ellipse center, and axis rotation relative to the transducer normal. The carotid width across multiple rotation angles is compared to acceptable diameters. For example, if diameters are greater 4 cm, 3 cm, or even 2 cm, then the system recommends which way the transducer should be rotated in roll or pitch.

Figure 19A:
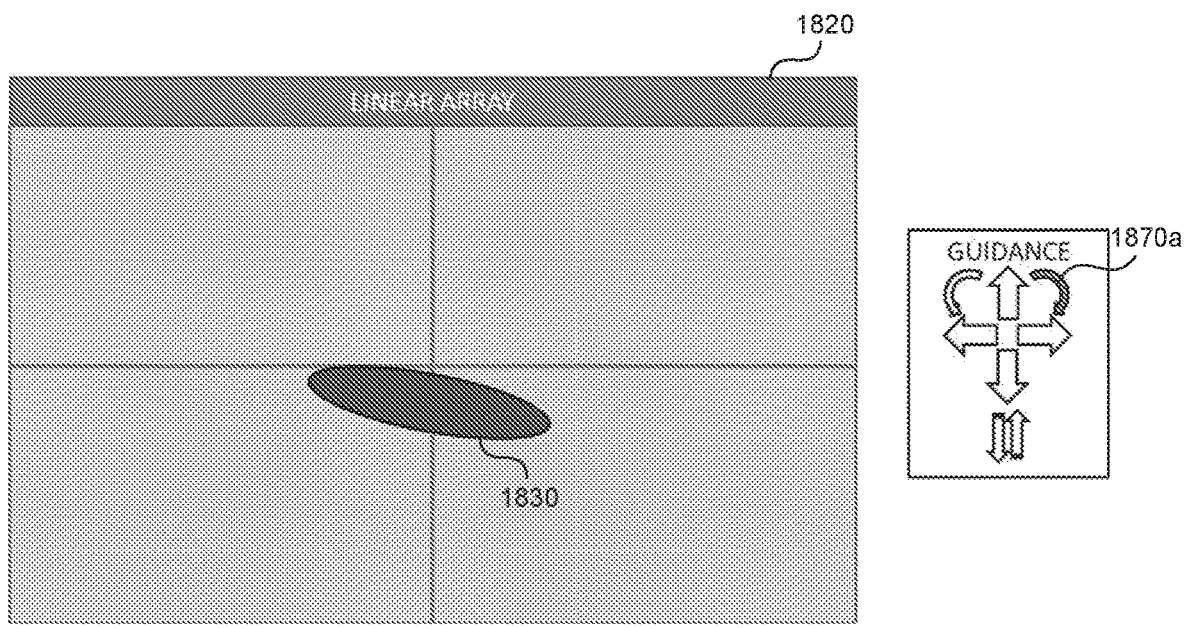
FIG. 19a-19c show a carotid in an imaging plane and a user interface on a transducer showing how the carotid appears in the image if a user moves the transducer in a roll direction indicated by the user interface in accordance with some embodiments of the disclosed technology.
Figure 19B:
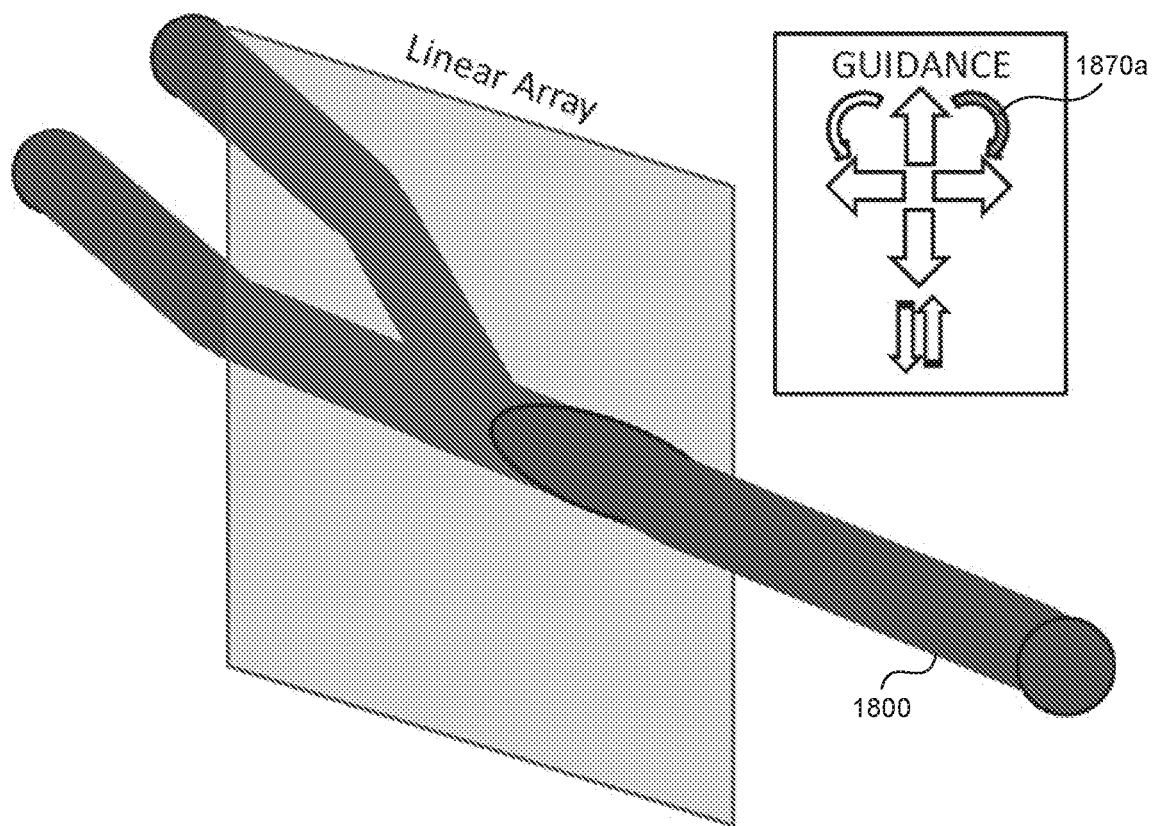
Figure 19C:
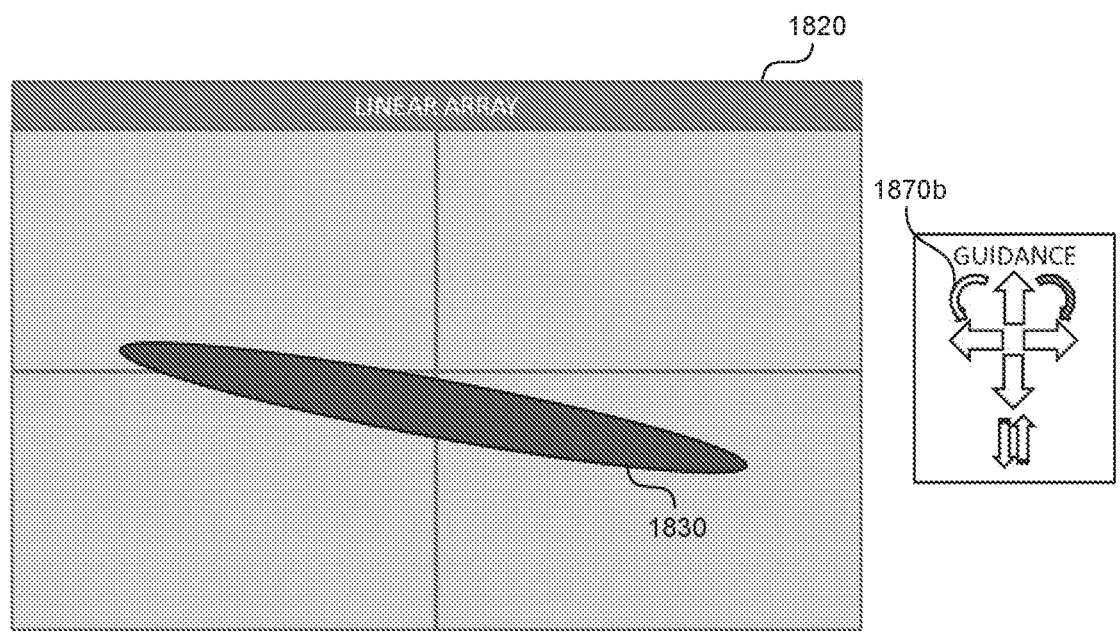

Ovality is another important parameter. Ovality determines whether the transducer is measuring mostly in the longitudinal dimension. In this case, the minor axis of the ellipse to best fit the carotid is much smaller than the major axis. High ovality may be due to poor roll or pitch rotation. After the images are processed and the ovality determined, the algorithm running on the processor compares the detected ovality to either an ideal ovality, a previous measured ovality, or other previously acquired images and recommends that the operator rotate the transducer in the azimuth (e.g. roll) dimension (see FIG. 19a). In one embodiment, the recommended translation or rotation is communicated to the operator by illuminating one or more visual indicators 1870a on the transducer handle. In another embodiment, the recommended translation or rotation is communicated to the operator through audible cues or commands. Once an optimal position is achieved based on the ovality calculation in the processor, the processor illuminates a separate indicator or uses another audible cue. This is because the longer axis is primarily in the lateral dimension which suggests a poor roll angle. In FIG. 19a, the right roll angle indicator 1870a is green which recommends to the user to rotate the transducer to the right. As the transducer is rotated in roll, the direction of the rotation may or may not be in the correct direction. FIG. 19b shows the resulting imaging plane 1910 hitting the carotid 1800. The resulting image 1830 shows an increasing ovality which signifies to the system to recommend rotation in the opposite direction (FIG. 19c).

Figure 20A:
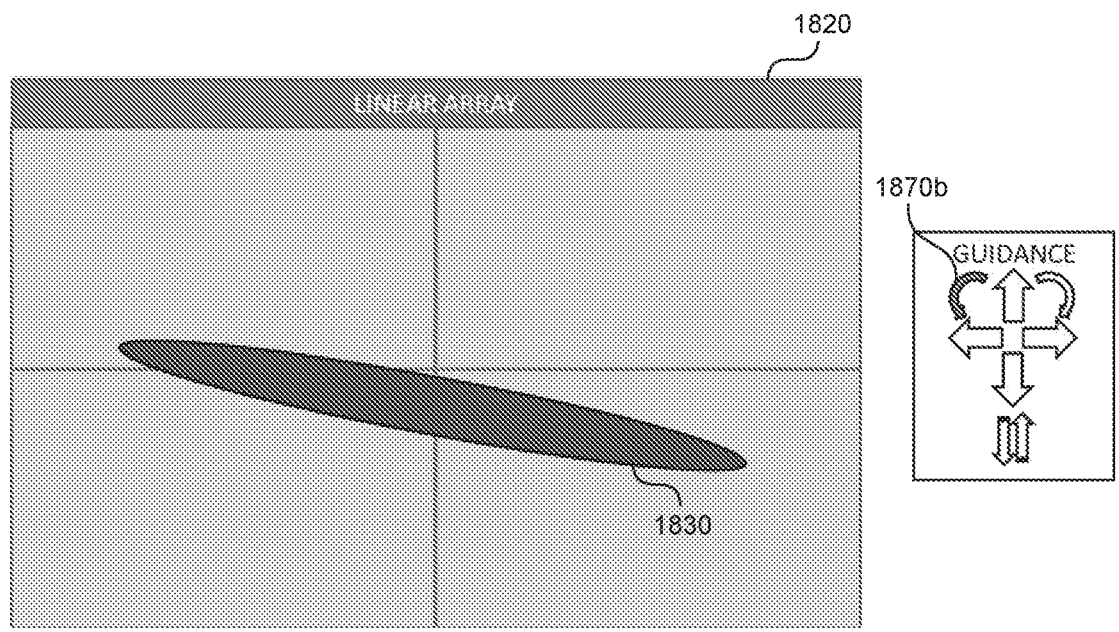
FIGS. 20a-20c show how a carotid in an image can be moved into a correction location within the image with directions on a user interface in accordance with some embodiments of the disclosed technology.
Figure 20B:
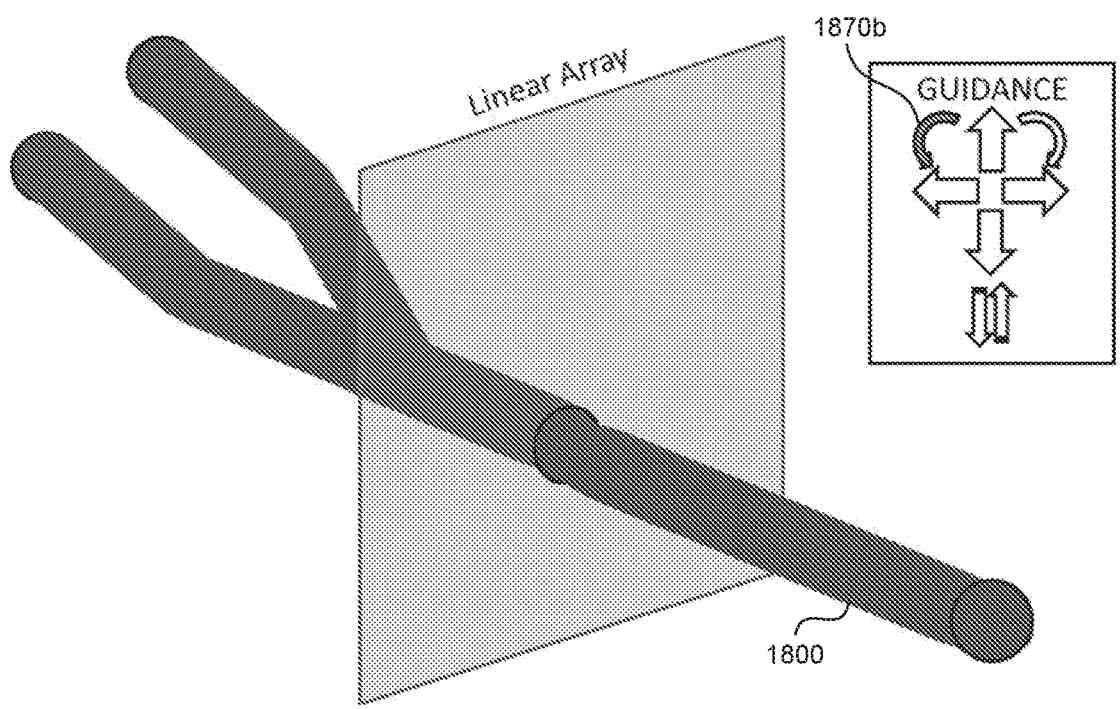
Figure 20C:
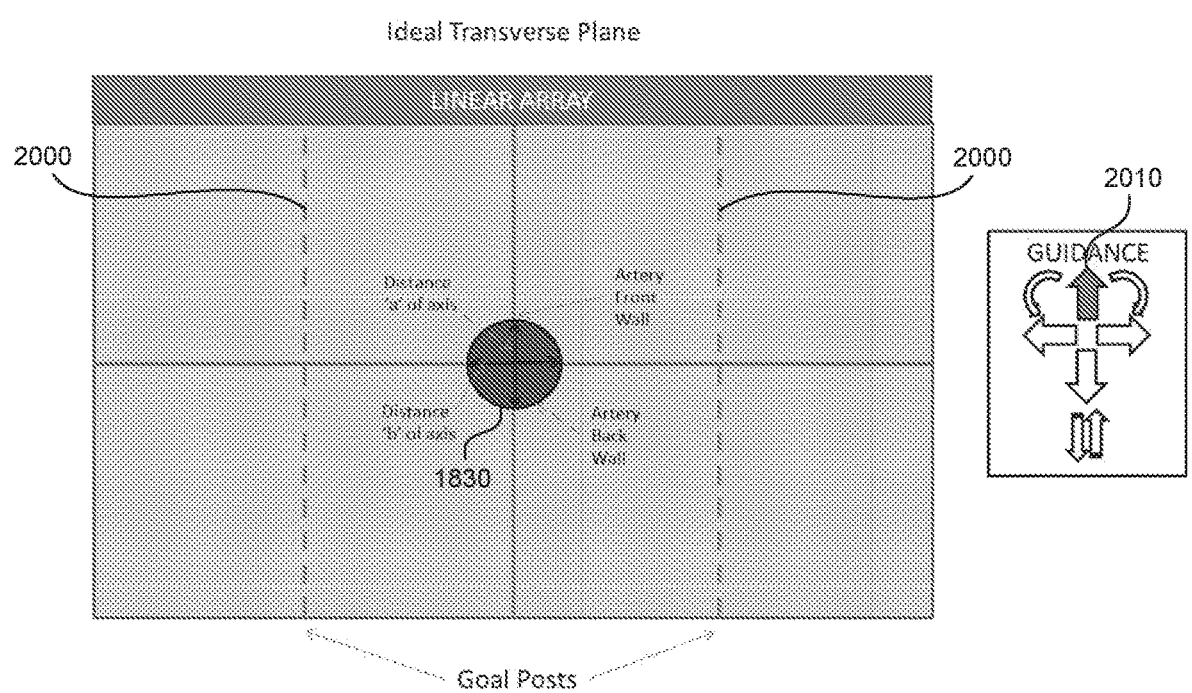

In one embodiment, when the processor computes the ovality and the determines rotating in the other direction (FIG. 20a) yields the optimal transducer position, then the processor turns off the illumination of the right roll arrow and turns on the left roll arrow 1870b. Other colors, audible or tactile cues may be used. As the transducer is rotated in the other direction, the carotid cross-section ovality improves to an acceptable value (FIG. 20b). The resulting ultrasound image is captured in FIG. 20c where the carotid cross-section 1830 is circular where the ovality is zero. Obviously, carotids are not going to be circularly symmetric, therefore, acceptable ovality may be an absolute value which is less than 5, 4, 3, 2, 1, 0.5 or 0.25. FIG. 20c also shows the image goal posts 2000 which signifies that the optimal resolution is being used for the acquisition. In addition to ovality, the contrast between the wall and lumen should be maximized. This can be accomplished by asking the user to tip the transducer in elevation to determine if the ideal angle is being used. Once these criteria have been sufficiently satisfied the manual 3D scanning can begin which recommended by the green elevation arrow 2010 shown in FIG. 20c.

Recall the transducer has position tracking information, so as frames are recorded, they can be spatially registered to each other to ensure a sufficient length of the carotid is acquired including the bifurcation. In some embodiments, the processor recalls previous studies and calculates the correlation with the currently acquired ultrasound images, the location of the current ultrasound images relative to the previous studies guides the operator on how to translate and rotate the transducer to acquire the best images. Furthermore, the system can determine whether the recommended carotid length has been acquired. If this scan is insufficient or if some frames along the longitudinal axis are insufficient, then the transducer may be moved back in the other direction to acquire additional data. Furthermore, depending on the spatial registration technology, the transducer may also be lifted off the skin. The registration system permits the appropriate spatial orientation and integration to previously acquired images. The same guidance system is used to help the operator keep the carotid within the goal posts as shown in FIG. 20c and maintain acceptable roll and pitch angles. Again colors, audible or tactile cues may be used in the guidance. Images are thrown out if certain criteria as previously covered are not satisfied or if enough frames in a region have already been captured. If as the transducer is dragged manually over the carotid and the acquired length is insufficient, then the guidance system may recommend to the operator to move back over the carotid to acquire a sufficient carotid length which may be 3 cm, 4 cm, 5 cm. The additional scan length improves the probability of making the right diagnosis. The bifurcation is a natural stopping point for one end of the exam. The exam may end 3 cm, 2 cm, 1 cm, or right at the start of the bifurcation. In one embodiment, the processor computes the one or more ideal ultrasound steering angles to maximize the echo from the vessel wall and the contrast between the vessel wall and the lumen based on the current image. The adaptive steering angle computed by the processor for the carotid wall improves the image quality and the rate at which rf data is acquired as well as how quickly the system adapts the transmit foci and image vectors. The scan of the carotid may also be done multiple times in one session to improve the likelihood that optimal frames along the entire longitudinal axis of the carotid are acquired. If the frame offers improved contrast or other characteristics over previously acquired data, then it may be averaged with the existing data or just replace the existing data.

Figure 21A:
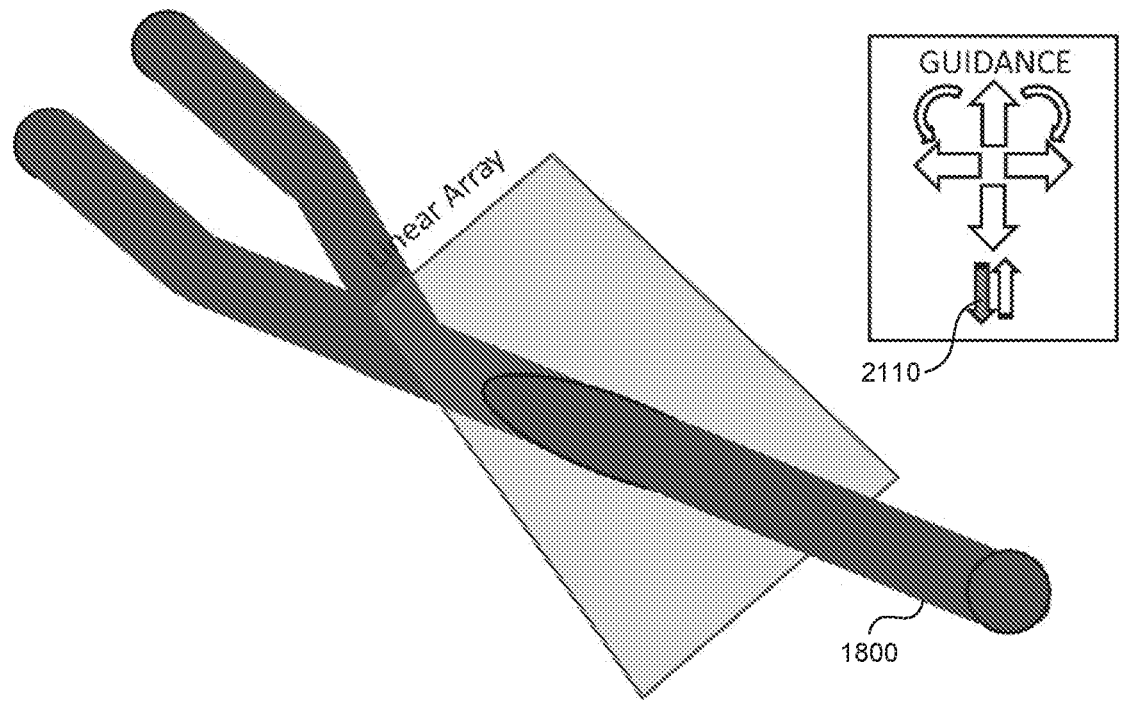
FIGS. 21a-21b show how a carotid appears in an image with an ovality in the major axis in the depth direction and how the user interface suggests rotation of the transducer in accordance with some embodiments of the disclosed technology.
Figure 21B:
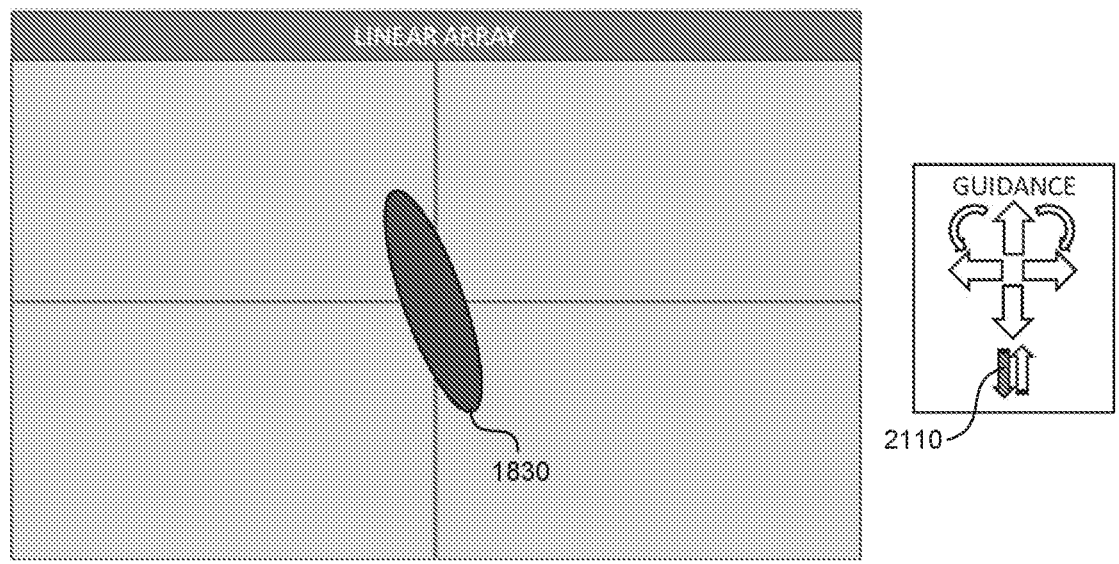

Although the previous section described a roll angle which caused high ovality, another situation can also cause significant difference between the major and minor axes. If the transducer is tilted in the elevation direction, then the major axis in the depth dimension is considerably larger than in the lateral dimension. This would also limit the contrast between the wall and the lumen because of the ultrasound angle of incidence to the wall. FIG. 21a diagrams the imaging plane of the transducer intersecting the carotid in this case. The resulting imaging plane is shown in FIG. 21b where the major axis of the carotid is more along the depth axis. The system recommends to the user to tilt the transducer back, so it is more normal with the longitudinal axis of the carotid. If this slight movement which is tracked through the position registration system leads to greater ovality, then a pitch arrow 2110 turns red or another color to stop and the other pitch arrow turns green to tilt the other direction.

Although the host computer which is sometimes referred to as the processor in this disclosure, the execution of the described methods may take place through other means. In one embodiment, one or more field programmable gate arrays (FPGAs) processes the ultrasound rf data, generates the images, analyzes the images according to the detailed description, and controls light and audible sensors to support the transducer movement. In another embodiment, FPGA and processors are used. In yet another embodiment, local hardware and cloud computing services are used to implements the analysis methods described in this disclosure. Furthermore, it is not necessary that the ultrasound image data processed by the processors or FPGA be ready for display. For example, pre-scan converted ultrasound data may be stored in memory and analyzed for the location of a vessel of interest such as the CCA. Therefore, the term ultrasound image data is meant to include more than image data that is ready to be displayed on a video monitor.

The user interface used to communicate the translation and rotation of the transducer to the operator is shown if FIGS. 18a through 21b. In one embodiment, the user interface for transducer translation and rotation is on a display connected to the system. In another embodiment, the user interface for transducer translation and rotation is on the transducer handle and consists of LEDs, lights, tactile actuators or a small screen (e.g. OLED). In one embodiment, the user interface includes indicators for transducer translation in one or more dimensions and one or more rotations. In another embodiment, the user interface only includes indicators for transducer in one or more dimensions. In another embodiment, the interface includes one or more indicators for translation orthogonal to the imaging plane (elevation) or translation in the lateral dimension within the imaging plane (azimuth) or translation in the depth dimension within the imaging plane. In one embodiment, the interface includes one or more indicators for rotation about the axis orthogonal to the imaging plane (yaw) or rotation about the axis which contains the centers of the linear array elements (pitch) or rotation about the axis which is orthogonal to the transducer face (roll).

We claim:

1. An ultrasound system configured to guide ultrasound acquisition in an individual, comprising:
    a handheld transducer configured to direct ultrasound signals towards tissue and to detect corresponding echo signals from the tissue;
    processing circuitry operably coupled to the handheld transducer and configured to execute program instructions to produce ultrasound image data from the detected echo signals and analyze the image data via the processing circuitry, wherein analyzing the image data comprises:
        (i) defining a region of interest from the tissue;
        (ii) identifying an artery from the region of interest as the echo signals are being acquired, based on:
            a brightness of a wall of the artery,
            a darkness in a lumen of the artery, and
            a difference between the brightness of the artery wall and the darkness of the artery lumen; and
        (iii) measuring at the region of interest, one or more thicknesses of constituent layers of the artery wall as the echo signals are being acquired.

2. The ultrasound system of claim 1, wherein analyzing the image data further comprises identifying an atheroma or an onset of an atheroma in the region of interest based on the one or more thicknesses of the constituent layers of the artery wall.

3. The ultrasound system of claim 1, wherein the processing circuitry is further configured to execute instructions to control a user interface that indicates a direction to a user to manually change a position or orientation of the handheld transducer to position the artery in a desired location in the image data.

4. The ultrasound system of claim 3, wherein the user interface is located on a video monitor on which the image data is displayed.

5. The ultrasound system of claim 3, wherein the user interface is located on the handheld transducer.

6. The ultrasound system of claim 3, wherein the user interface includes first indicators to move the handheld transducer in at least one of (i) a left/right direction or (ii) an up/down direction, and second indicators to change at least one of (i) a pitch of the handheld transducer or (ii) a roll of the handheld transducer.

7. The ultrasound system of claim 1, wherein analyzing the image data further comprises analyzing an ovalness of the artery in the image data.

8. The ultrasound system of claim 1, wherein the processing circuitry is further configured to execute instructions to control a user interface that indicates a direction to a user to manually change a position or orientation of the handheld transducer such that the artery has a minimal ovalness and is positioned at or near a center of the image data.

9. The ultrasound system of claim 1, wherein the processing circuitry is further configured to execute instructions to store a sequence of the image data where the artery is in a desired location in the image data.

10. The ultrasound system of claim 1, wherein the region of interest is a first region of interest, and wherein analyzing the image data further comprises defining a second region of interest smaller than and within the first region of interest.

11. The ultrasound system of claim 10, wherein analyzing the image data further comprises identifying an atheroma or an onset of an atheroma in the second region of interest based on the one or more thicknesses of the constituent layers of the artery wall.

12. A method for guiding ultrasound acquisition in an individual, the method comprising:
    directing ultrasound signals towards a tissue;
    detecting corresponding echo signals from the tissue;
    producing ultrasound image data from the detected echo signals; and
    analyzing the image data, wherein analyzing the image data comprises:
        (i) defining a region of interest from the tissue;
        (ii) identifying an artery from the region of interest as the echo signals are being acquired, based on:
            a brightness of a wall of the artery,
            a darkness in a lumen of the artery, and
            a difference between the brightness of the artery wall and the darkness of the artery lumen; and
        (iii) measuring at the region of interest, one or more thicknesses of constituent layers of the artery wall as the echo signals are being acquired.

13. The method of claim 12, wherein the method further comprises analyzing the image data by identifying an onset of an atheroma in the region of interest based on the one or more thicknesses of constituent layers of the artery wall.

14. The method of claim 12, wherein the method further comprises controlling a user interface that indicates a direction to the user to redirect the ultrasound signals towards the tissue to position the artery in a desired location in the image data.

15. The method of claim 12, wherein the method further comprises:
    analyzing the image data by analyzing an ovalness of the artery in the image data; and
    controlling a user interface that indicates a direction to the user to redirect the ultrasound signals towards the tissue such that the artery has a minimal ovalness and is positioned at or near a center of the image data.

16. The method of claim 12, wherein the method further comprises storing a sequence of the image data where the artery is in a desired location in the image data.

17. The method of claim 12, wherein the region of interest is a first region of interest, and wherein the method further comprises analyzing the image data by defining a second region of interest smaller than and within the first region of interest.

18. The method of claim 17, wherein the method further comprises analyzing the image data by identifying an atheroma or an onset of an atheroma in the second region of interest based on the one or more thicknesses of constituent layers of the artery wall.

\* \* \* \* \*